United States Patent
Jeffrey et al.

(10) Patent No.: US 11,993,584 B2
(45) Date of Patent: May 28, 2024

(54) SOLID FORMS OF AN AZOLOPYRIMIDINE COMPOUND

(71) Applicant: ARCUS BIOSCIENCES, INC., Hayward, CA (US)

(72) Inventors: Jenna Leigh Jeffrey, Oakland, CA (US); Manmohan Reddy Leleti, Dublin, CA (US); Dillon Harding Miles, Berkeley, CA (US); Jay Patrick Powers, Pacifica, CA (US)

(73) Assignee: ARCUS BIOSCIENCES, INC., Hayward, CA (US)

( * ) Notice: Subject to any disclaimer, the term of this patent is extended or adjusted under 35 U.S.C. 154(b) by 689 days.

(21) Appl. No.: 17/260,847

(22) PCT Filed: Jul. 17, 2019

(86) PCT No.: PCT/US2019/042226
§ 371 (c)(1),
(2) Date: Jan. 15, 2021

(87) PCT Pub. No.: WO2020/018680
PCT Pub. Date: Jan. 23, 2020

(65) Prior Publication Data
US 2021/0269422 A1    Sep. 2, 2021

Related U.S. Application Data

(60) Provisional application No. 62/700,064, filed on Jul. 18, 2018.

(51) Int. Cl.
*C07D 401/14* (2006.01)
*A61K 45/06* (2006.01)
*C07K 16/28* (2006.01)

(52) U.S. Cl.
CPC .......... *C07D 401/14* (2013.01); *A61K 45/06* (2013.01); *C07K 16/2818* (2013.01); *C07K 16/2827* (2013.01); *C07B 2200/13* (2013.01)

(58) Field of Classification Search
CPC ................................................ C07D 401/14
See application file for complete search history.

(56) References Cited

U.S. PATENT DOCUMENTS

| | | | |
|---|---|---|---|
| 4,474,599 A | 10/1984 | Rogers et al. | |
| 10,399,962 B2 | 9/2019 | Beatty et al. | |
| 2005/0026963 A1 | 2/2005 | Cosford et al. | |
| 2015/0239866 A1 | 8/2015 | Machacek et al. | |
| 2018/0215730 A1 | 8/2018 | Beatty et al. | |
| 2021/0101880 A1 | 4/2021 | Beatty et al. | |
| 2022/0144808 A1 | 5/2022 | Beatty et al. | |
| 2022/0211701 A1 | 7/2022 | Anderson et al. | |
| 2022/0235031 A1 | 7/2022 | Leleti et al. | |
| 2022/0241313 A1 | 8/2022 | Tan et al. | |

FOREIGN PATENT DOCUMENTS

| | | |
|---|---|---|
| UY | 37574 A | 5/2018 |
| WO | 2010/077582 A1 | 7/2010 |
| WO | WO-2010077582 A1 | 1/2015 |
| WO | WO-2015008872 A1 | 1/2015 |
| WO | 2019/161054 A1 | 8/2019 |

OTHER PUBLICATIONS

International Search Report for PCT/US2019/042226, dated Sep. 30, 2019, 3 pages.
Written Opinion for PCT/US2019/042226, dated Sep. 30, 2019, 6 pages.
Caira, M. R., Crystalline Polymorphism of Organic Compounds, Topics in Current Chemistry, vol. 198, Springer Verlag Berlin Heidelberg 1998, pp. 163-208, XP008166276.
Extended European Search Report for European Application No. 19838123.8 dated Feb. 28, 2022. 8 pages.
Farumashia, 2016, vol. 52 , No. 5 , pp. 387 391.
Seitz et al., Safety, tolerability, and pharmacology of AB928, a novel dual adenosine receptor antagonist, in a randomized, phase 1 study in healthy volunteers, Investigational New Drugs (2019) 37:711-721.

*Primary Examiner* — Rebecca L Anderson
(74) *Attorney, Agent, or Firm* — Sheppard Mullin Richter & Hampton LLP

(57) ABSTRACT

The present invention provides solid forms, solvates and hydrates of 3-[2-amino-6-(1-{[6-(2-hydroxypropan-2-yl)pyridin-2-yl]methyl}-1H-1,2,3-triazol-4-yl)pyrimidin-4-yl]-2-methylbenzonitrile (Compound I), (I)

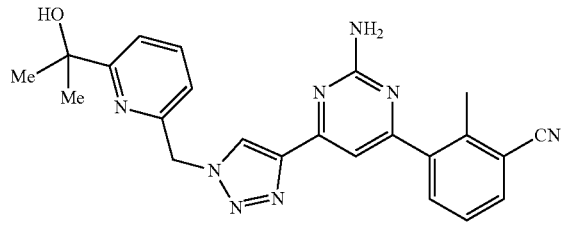

and methods of making and using the same.

21 Claims, 8 Drawing Sheets

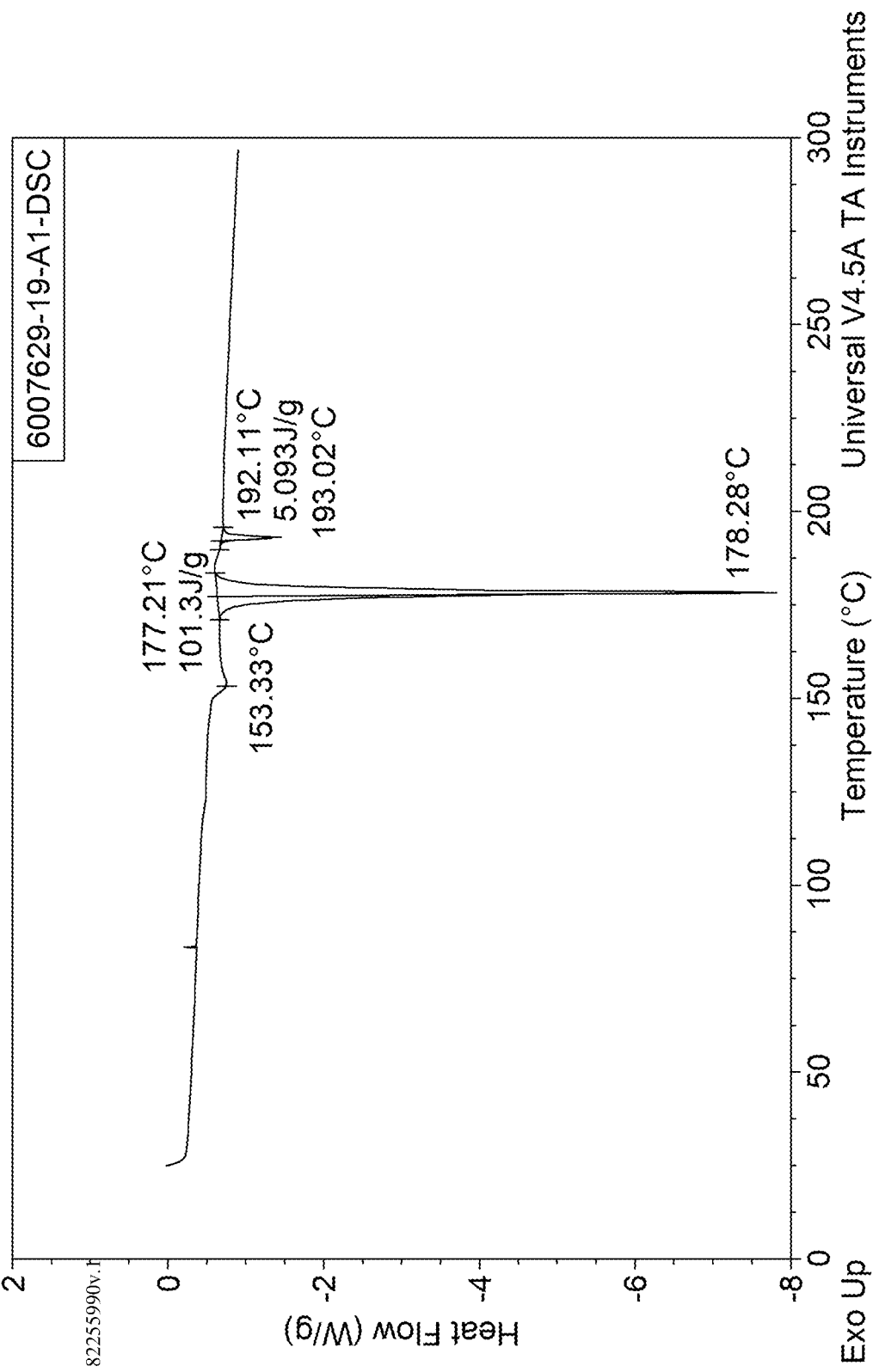

SOLID FORMS OF AN AZOLOPYRIMIDINE COMPOUND

CROSS-REFERENCES TO RELATED APPLICATIONS

This application is the U.S. National Stage entry under § 371 of International Application No. PCT/US2019/042226, filed Jul. 17, 2019, which claims the benefit of priority to U.S. Provisional Application No. 62/700,064, filed Jul. 18, 2018, the contents of which are herein incorporated by reference for all purposes.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Adenosine is a purine nucleoside compound comprising a complex of adenine and a ribose sugar molecule (ribofuranose). Adenosine occurs naturally in mammals and plays important roles in several biochemical processes, including energy transfer (as adenosine triphosphate and adenosine monophosphate) and signal transduction (as cyclic adenosine monophosphate). Adenosine also serves in processes associated with vasodilation, including cardiac vasodilation, and acts as a neuromodulator (e.g., it is thought to be involved in promoting sleep). In addition to its involvement in these biochemical processes, adenosine is used as a therapeutic antiarrhythmic agent to treat, for example, supraventricular tachycardia. As discussed further herein, tumors evade host responses by inhibiting immune function and promoting tolerance, and adenosine has been shown to play an important role in mediating tumor evasion of the immune system. Adenosine signaling through $A_{2A}Rs$ and $A_{2B}Rs$, expressed on a variety of immune cell subsets and endothelial cells, has been established as having an important role in protecting tissues during inflammatory responses. As such, under certain conditions adenosine protects tumors from immune destruction (see, e.g., Fishman, P, et al. (2009) Handb Exp Pharmacol 193:399-441).

The adenosine receptors are a class of purinergic G protein-coupled receptors with adenosine as the endogenous ligand. The four types of adenosine receptors in humans are referred to as $A_1$, $A_{2A}$, $A_{2B}$ and $A_3$. Modulation of $A_1$ has been proposed for the management and treatment of, for example, neurological disorders, asthma, and heart and renal failure; $A_{2A}$ antagonists have been proposed for the management and treatment of, for example, Parkinson's disease; modulation of $A_{2B}$ has been proposed for the management and treatment of, for example, chronic pulmonary diseases, including asthma; and modulation of $A_3$ has been proposed for the management and treatment of, for example, asthma and chronic obstructive pulmonary diseases, glaucoma, cancer, and stroke.

Historically, modulators of adenosine receptors have been nonselective. This is acceptable in certain indications, such as where the endogenous agonist adenosine, which acts on all four adenosine receptors in cardiac tissue, is administered parenterally for the treatment of severe tachycardia. However, the use of sub-type selective adenosine receptor agonists and antagonists provides the potential for achieving desired outcomes while minimizing or eliminating adverse effects.

The compound 3-[2-amino-6-(1-{[6-(2-hydroxypropan-2-yl)pyridin-2-yl]methyl}-1H-1,2,3-triazol-4-yl)pyrimidin-4-yl]-2-methylbenzonitrile, designated herein as Compound I, as described for example in U.S. patent application Ser. No. 15/875,106 and PCT application no. PCT/US18/14352, has been reported to be a sub-type selective adenosine receptor antagonist. Compound I is a potent antagonist of $A_{2A}R$ and $A_{2B}R$ with a potency on both receptors of less than 10 nM. There is a need for stable solid forms of Compound I that can be used in pharmaceutical compositions.

BRIEF SUMMARY OF THE INVENTION

The present invention relates to solid forms of compounds that modulate the adenosine $A_{2A}$ receptor ($A_{2A}R$) and/or the adenosine $A_{2B}$ receptor ($A_{2B}R$), and compositions (e.g., pharmaceutical compositions) comprising the compounds. Such compounds, including methods of their synthesis, and compositions are described in detail below.

In some embodiments, the present invention provides a solid form of a compound having the formula:

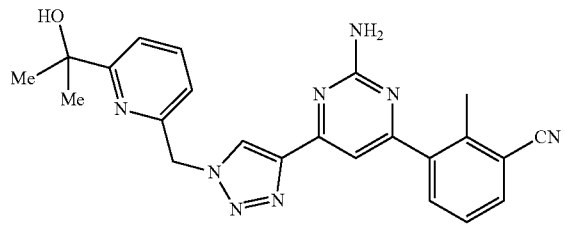 [SMILES: Cc1c(C#N)cccc1-c1cc(-c2cn(Cc3cccc(C(C)(C)O)n3)nn2)nc(N)n1]

(Compound I)

or a hydrate or solvate thereof.

In some embodiments, the present invention provides a solid Form I of Compound I, or a solvate or hydrate thereof, characterized by an X-ray powder diffraction (XRPD) pattern comprising one or more peaks at 6.9, 8.0, 8.2, 12.5, 12.7, 14.8, 15.0, 15.7, 16.8, 18.1, 18.8, 19.2, 20.6, 21.1, 21.8, 24.9, 27.1, or 27.7 degrees 2θ (±0.1 degrees 2θ), wherein the XRPD is made using $CuK_{\alpha 1}$ radiation.

The present invention further provides a method of preparing a solid Form I of Compound I by forming a mixture of Compound I, and a solvent comprising a $C_3$-$C_5$ ketone, dichloromethane, or toluene, under conditions suitable to prepare Form I.

Additionally, provided are pharmaceutical compositions comprising the solid forms described herein.

Further provided herein are methods of treating a disease, disorder, or condition mediated at least in part by the adenosine $A_{2A}$ receptor ($A_{2A}R$) or the adenosine $A_{2B}$ receptor ($A_{2B}R$), comprising administering to a subject in need thereof a therapeutically effective amount of a solid form of Compound I. In some embodiments, the disease, disorder, or condition is cancer, which can be treated with the solid form of Compound I alone or in combination with other therapeutic agents, such as an immune checkpoint inhibitor.

BRIEF DESCRIPTION OF THE DRAWINGS

FIG. 8 shows a differential scanning calorimetry (DSC) plot of Compound I Form III.

DETAILED DESCRIPTION OF THE INVENTION

Figure 1:
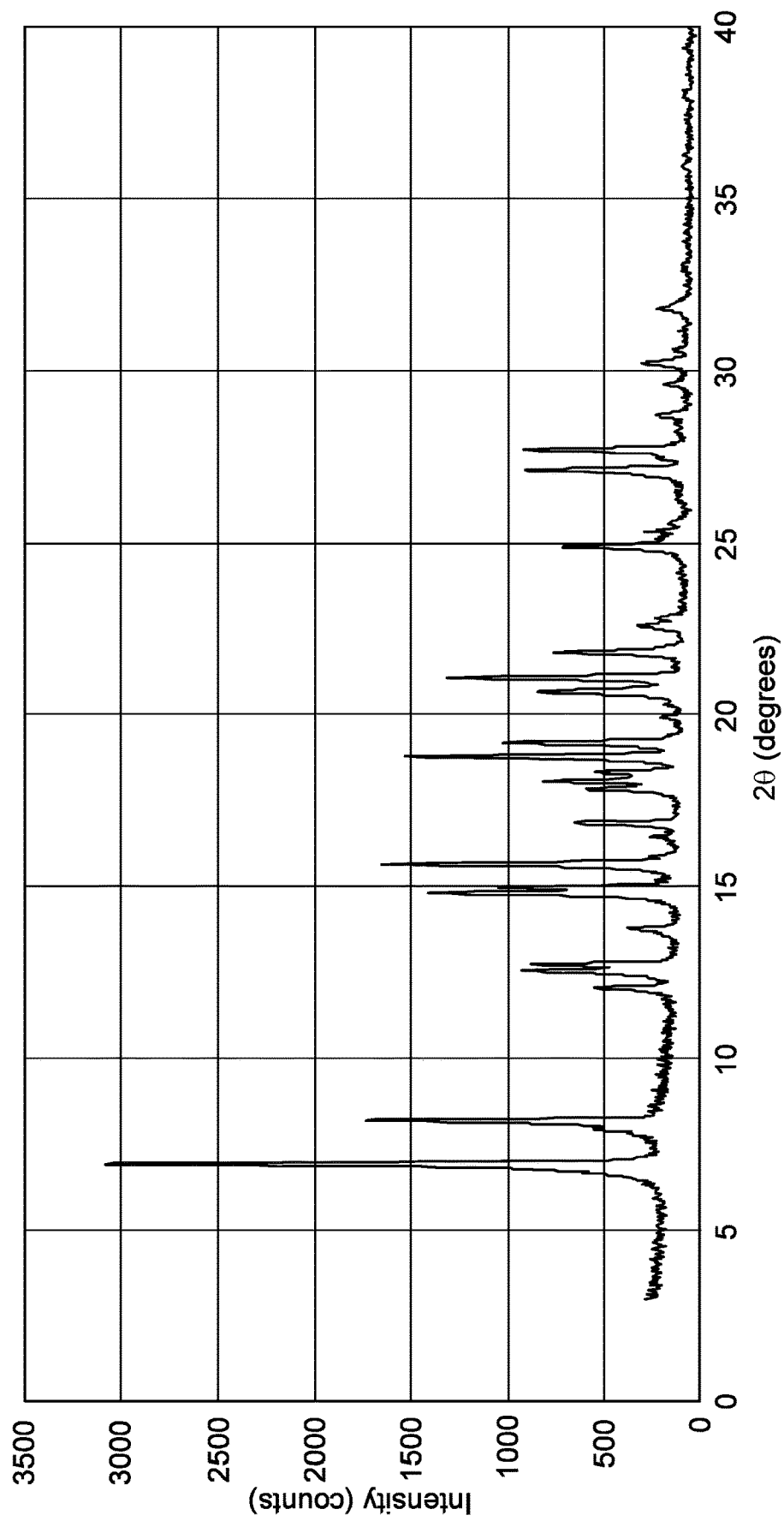
FIG. 1 shows an X-ray powder diffraction (XRPD) pattern of Compound I Form I.

Before the present invention is further described, it is to be understood that the invention is not limited to the particular embodiments set forth herein, and it is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs.

As used herein, the singular forms "a," "an," and "the" include plural referents unless the context clearly dictates otherwise. It is further noted that the claims may be drafted to exclude any optional element. As such, this statement is intended to serve as antecedent basis for use of such exclusive terminology such as "solely," "only" and the like in connection with the recitation of claim elements, or use of a "negative" limitation.

The publications discussed herein are provided solely for their disclosure prior to the filing date of the present application. Further, the dates of publication provided may be different from the actual publication dates, which may need to be independently confirmed.

General

The compound 3-[2-amino-6-(1-{[6-(2-hydroxypropan-2-yl)pyridin-2-yl]methyl}-1H-1,2,3-triazol-4-yl)pyrimidin-4-yl]-2-methylbenzonitrile (Compound I) is a selective and potent antagonist of the adenosine $A_{2A}$ receptor ($A_{2A}R$) and/or the adenosine $A_{2B}$ receptor ($A_{2B}R$):

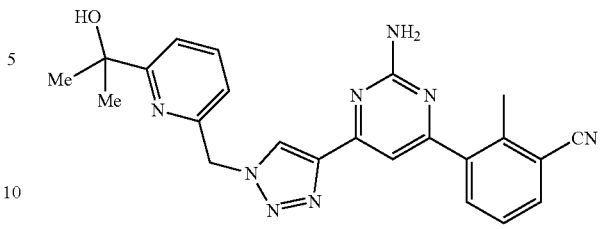

(Compound I)

The present invention results from the surprising discoveries of the solid forms of Compound I, advantages attributed to the forms as described herein, and processes for making the solid forms. Crystalline materials are generally more stable physically and chemically. The superior stability of crystalline material may make them more suitable to be used in the final dosage form as shelf life of the product is directly correlated with stability. A crystallization step in active pharmaceutical ingredient (API) processing also means an opportunity to upgrade the drug substance purity by rejecting the impurities to the processing solvent.

Definitions

Unless otherwise indicated, the following terms are intended to have the meaning set forth below. Other terms are defined elsewhere throughout the specification.

"Hydrate" refers to a complex formed by the combining of Compound I and water. The term includes stoichiometric as well as non-stoichiometric hydrates.

"Solvate" refers to a complex formed by the combining of Compound I and a solvent.

"Desolvated" refers to a Compound I form that is a solvate as described herein, and from which solvent molecules have been partially or completely removed. Desolvation techniques to produce desolvated forms include, without limitation, exposure of a Compound I Form (solvate) to a vacuum, subjecting the solvate to elevated temperature, exposing the solvate to a stream of gas, such as air or nitrogen, or any combination thereof. Thus, a desolvated Compound I form can be anhydrous, i.e., completely without solvent molecules, or partially solvated wherein solvent molecules are present in stoichiometric or non-stoichiometric amounts.

"Alcohol" refers to a solvent having a hydroxy group. Representative alcohols can have any suitable number of carbon atoms, such as $C_1$-$C_6$, and any suitable number of hydroxy groups, such as 1-3. Exemplary alcohols include, but are not limited to, methanol, ethanol, n-propanol, i-propanol, etc.

"Substantially free of other crystalline forms of Compound I" refers to a crystalline form of Compound I that contains less than 10% of other crystalline forms of Compound I. For example, substantially free can refer to a crystalline form of Compound I that contains less than 9, 8, 7, 6, 5, 4, 3, 2, or 1% of other crystalline forms of Compound I. Preferably, substantially free refers to a crystalline form of Compound I that contains less than 5% of other crystalline forms of Compound I. Preferably, substantially free refers to a crystalline form of Compound I that contains less than 1% of other crystalline forms of Compound I.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The compounds of the present invention may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3$H), iodine-125 ($^{125}$I) or carbon-14 ($^{14}$C), or non-radioactive isotopes, such as deuterium ($^2$H) or carbon-13 ($^{13}$C). Such isotopic variations can provide additional utilities to those described elsewhere within this application. For instance, isotopic variants of the compounds of the invention may find additional utility, including but not limited to, as diagnostic and/or imaging reagents, or as cytotoxic/radiotoxic therapeutic agents. Additionally, isotopic variants of the compounds of the invention can have altered pharmacokinetic and pharmacodynamic characteristics which can contribute to enhanced safety, tolerability or efficacy during treatment. All isotopic variations of the compounds of the present invention, whether radioactive or not, are intended to be encompassed within the scope of the present invention.

The terms "patient" or "subject" are used interchangeably to refer to a human or a non-human animal (e.g., a mammal).

The terms "administration", "administer" and the like, as they apply to, for example, a subject, cell, tissue, organ, or biological fluid, refer to contact of, for example, an inhibitor of $A_{2A}R/A_{2B}R$, a pharmaceutical composition comprising same, or a diagnostic agent to the subject, cell, tissue, organ, or biological fluid. In the context of a cell, administration includes contact (e.g., in vitro or ex vivo) of a reagent to the cell, as well as contact of a reagent to a fluid, where the fluid is in contact with the cell.

The terms "treat", "treating", treatment" and the like refer to a course of action (such as administering an inhibitor of $A_{2A}R/A_{2B}R$ or a pharmaceutical composition comprising same) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject. Thus, treatment includes inhibiting (e.g., arresting the development or further development of the disease, disorder or condition or clinical symptoms association therewith) an active disease.

The term "in need of treatment" as used herein refers to a judgment made by a physician or other caregiver that a subject requires or will benefit from treatment. This judgment is made based on a variety of factors that are in the realm of the physician's or caregiver's expertise.

The terms "prevent", "preventing", "prevention" and the like refer to a course of action (such as administering an $A_{2A}R/A_{2B}R$ inhibitor or a pharmaceutical composition comprising same) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other caregiver that a subject requires or will benefit from preventative care. This judgment is made based on a variety of factors that are in the realm of a physician's or caregiver's expertise.

The phrase "therapeutically effective amount" refers to the administration of an agent to a subject, either alone or as part of a pharmaceutical composition and either in a single dose or as part of a series of doses, in an amount capable of having any detectable, positive effect on any symptom, aspect, or characteristic of a disease, disorder or condition when administered to the subject. The therapeutically effective amount can be ascertained by measuring relevant physiological effects, and it can be adjusted in connection with the dosing regimen and diagnostic analysis of the subject's condition, and the like. By way of example, measurement of the serum level of an $A_{2A}R/A_{2B}R$ inhibitor (or, e.g., a metabolite thereof) at a particular time post-administration may be indicative of whether a therapeutically effective amount has been used.

The terms "inhibitors" and "antagonists", or "activators" and "agonists" refer to inhibitory or activating molecules, respectively, for example, for the activation of, e.g., a ligand, receptor, cofactor, gene, cell, tissue, or organ. Inhibitors are molecules that decrease, block, prevent, delay activation, inactivate, desensitize, or down-regulate, e.g., a gene, protein, ligand, receptor, or cell. Activators are molecules that increase, activate, facilitate, enhance activation, sensitize, or up-regulate, e.g., a gene, protein, ligand, receptor, or cell. An inhibitor may also be defined as a molecule that reduces, blocks, or inactivates a constitutive activity. An "agonist" is a molecule that interacts with a target to cause or promote an increase in the activation of the target. An "antagonist" is a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist.

The terms "modulate", "modulation" and the like refer to the ability of a molecule (e.g., an activator or an inhibitor) to increase or decrease the function or activity of $A_{2A}R/A_{2B}R$, either directly or indirectly. A modulator may act alone, or it may use a cofactor, e.g., a protein, metal ion, or small molecule. Examples of modulators include small molecule compounds and other bioorganic molecules. Numerous libraries of small molecule compounds (e.g., combinatorial libraries) are commercially available and can serve as a starting point for identifying a modulator. The skilled artisan is able to develop one or more assays (e.g., biochemical or cell-based assays) in which such compound libraries can be screened in order to identify one or more compounds having the desired properties; thereafter, the skilled medicinal chemist is able to optimize such one or more compounds by, for example, synthesizing and evaluating analogs and derivatives thereof. Synthetic and/or molecular modeling studies can also be utilized in the identification of an Activator.

The "activity" of a molecule may describe or refer to the binding of the molecule to a ligand or to a receptor; to catalytic activity; to the ability to stimulate gene expression or cell signaling, differentiation, or maturation; to antigenic activity; to the modulation of activities of other molecules; and the like. The term "proliferative activity" encompasses an activity that promotes, that is necessary for, or that is specifically associated with, for example, normal cell division, as well as cancer, tumors, dysplasia, cell transformation, metastasis, and angiogenesis.

Solid Forms of Compound I

The present invention provides solid forms of compound 3-[2-amino-6-(1-{[6-(2-hydroxypropan-2-yl)pyridin-2-yl]methyl}-1H-1,2,3-triazol-4-yl)pyrimidin-4-yl]-2-methyl-benzonitrile (Compound I), including crystalline and amorphous forms, as well as solvate and hydrate forms. In some embodiments, the present invention provides a solid form, e.g., a crystalline form, of Compound I having the structure:

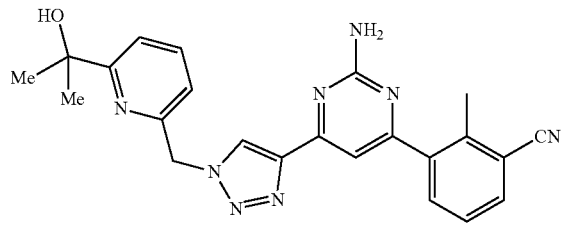

and solvates or hydrates thereof.

Compound I can adopt a variety of solid forms, including, but not limited to, Form I, Form II, and Form III. Compound I can form a mixture of two or more crystalline forms, or form a single crystalline form substantially free of other crystalline forms.

Form I

In some embodiments, solid Form I of Compound I can be characterized by an X-ray powder diffraction pattern (XRPD) having peaks at 6.9, 8.0, 8.2, 12.5, 12.7, 14.8, 15.0, 15.7, 16.8, 18.1, 18.8, 19.2, 20.6, 21.1, 21.8, 24.9, 27.1, or 27.7 degrees 2θ (±0.1 degrees 2θ), wherein the XRPD is made using $CuK_{\alpha 1}$ radiation, or a differential scanning calorimetry (DSC) plot having an endotherm at about 193° C., or both the aforementioned XRPD and DSC.

Form I of Compound I can be characterized by an X-ray powder diffraction (XRPD) pattern having one or more, e.g., two, three, four, five, or more, peaks at 6.9, 8.0, 8.2, 12.5, 12.7, 14.8, 15.0, 15.7, 16.8, 18.1, 18.8, 19.2, 20.6, 21.1, 21.8, 24.9, 27.1, or 27.7 degrees 2θ (±0.1 degrees 2θ), wherein the XRPD is made using $CuK_{\alpha 1}$ radiation. In some embodiments, the solid Form I of Compound I can be characterized by an X-ray powder diffraction pattern having two or more peaks at 6.9, 8.0, 8.2, 12.5, 12.7, 14.8, 15.0, 15.7, 16.8, 18.1, 18.8, 19.2, 20.6, 21.1, 21.8, 24.9, 27.1, or 27.7 degrees 2θ (±0.1 degrees 2θ), wherein the XRPD is made using $CuK_{\alpha 1}$ radiation. In some embodiments, the solid Form I of Compound I can be characterized by an X-ray powder diffraction pattern having three or more peaks at 6.9, 8.0, 8.2, 12.5, 12.7, 14.8, 15.0, 15.7, 16.8, 18.1, 18.8, 19.2, 20.6, 21.1, 21.8, 24.9, 27.1, or 27.7 degrees 2θ (±0.1 degrees 2θ), wherein the XRPD is made using $CuK_{\alpha 1}$ radiation. In some embodiments, the solid Form I of Compound I can be characterized by an X-ray powder diffraction pattern having four or more peaks at 6.9, 8.0, 8.2, 12.5, 12.7, 14.8, 15.0, 15.7, 16.8, 18.1, 18.8, 19.2, 20.6, 21.1, 21.8, 24.9, 27.1, or 27.7 degrees 2θ (±0.1 degrees 2θ), wherein the XRPD is made using $CuK_{\alpha 1}$ radiation. In some embodiments, the solid Form I of Compound I can be characterized by an X-ray powder diffraction pattern having five or more peaks at 6.9, 8.0, 8.2, 12.5, 12.7, 14.8, 15.0, 15.7, 16.8, 18.1, 18.8, 19.2, 20.6, 21.1, 21.8, 24.9, 27.1, or 27.7 degrees 2 (±0.1 degrees 2θ), wherein the XRPD is made using $CuK_{\alpha 1}$ radiation.

In some embodiments, the solid Form I of Compound I can be characterized by an X-ray powder diffraction pattern having six or more peaks at 6.9, 8.0, 8.2, 12.5, 12.7, 14.8, 15.0, 15.7, 16.8, 18.1, 18.8, 19.2, 20.6, 21.1, 21.8, 24.9, 27.1, or 27.7 degrees 2θ (±0.1 degrees 2θ), wherein the XRPD is made using $CuK_{\alpha 1}$ radiation. In some embodiments, the solid Form I of Compound I can be characterized by an X-ray powder diffraction pattern having seven or more peaks at 6.9, 8.0, 8.2, 12.5, 12.7, 14.8, 15.0, 15.7, 16.8, 18.1, 18.8, 19.2, 20.6, 21.1, 21.8, 24.9, 27.1, or 27.7 degrees 2θ (±0.1 degrees 2θ), wherein the XRPD is made using $CuK_{\alpha 1}$ radiation. In some embodiments, the solid Form I of Compound I can be characterized by an X-ray powder diffraction pattern having eight or more peaks at 6.9, 8.0, 8.2, 12.5, 12.7, 14.8, 15.0, 15.7, 16.8, 18.1, 18.8, 19.2, 20.6, 21.1, 21.8, 24.9, 27.1, or 27.7 degrees 2 (±0.1 degrees 2θ), wherein the XRPD is made using CuK$_{\alpha 1}$ radiation. In some embodiments, the solid Form I of Compound I can be characterized by an X-ray powder diffraction pattern having nine or more peaks at 6.9, 8.0, 8.2, 12.5, 12.7, 14.8, 15.0, 15.7, 16.8, 18.1, 18.8, 19.2, 20.6, 21.1, 21.8, 24.9, 27.1, or 27.7 degrees 2θ (±0.1 degrees 2θ), wherein the XRPD is made using CuK$_{\alpha 1}$ radiation. In some embodiments, the solid Form I of Compound I can be characterized by an X-ray powder diffraction pattern having ten or more peaks at 6.9, 8.0, 8.2, 12.5, 12.7, 14.8, 15.0, 15.7, 16.8, 18.1, 18.8, 19.2, 20.6, 21.1, 21.8, 24.9, 27.1, or 27.7 degrees 2 (±0.1 degrees 2θ), wherein the XRPD is made using CuK$_{\alpha 1}$ radiation.

In some embodiments, the solid Form I of Compound I can be characterized by an XRPD pattern having peaks at 6.9, 8.2, and 15.7 degrees 2θ (±0.1 degrees 2θ), wherein the XRPD is made using CuK$_{\alpha 1}$ radiation. In some embodiments, the solid Form I of Compound I can be characterized by an X-ray powder diffraction (XRPD) pattern further comprising one or more peaks at 14.8, 15.0, 18.8, or 21.1 degrees 2θ (±0.1 degrees 2θ), wherein the XRPD is made using CuK$_{\alpha 1}$ radiation. In some embodiments, the solid Form I of Compound I can be characterized by an X-ray powder diffraction (XRPD) pattern further comprising two or more peaks at 14.8, 15.0, 18.8, or 21.1 degrees 2θ (±0.1 degrees 2θ), wherein the XRPD is made using CuK$_{\alpha 1}$ radiation. In some embodiments, the solid Form I of Compound I can be characterized by an X-ray powder diffraction (XRPD) pattern further comprising three or more peaks at 14.8, 15.0, 18.8, or 21.1 degrees 2θ (±0.1 degrees 2θ), wherein the XRPD is made using CuK$_{\alpha 1}$ radiation.

In some embodiments, the solid Form I of Compound I can be characterized by an X-ray powder diffraction (XRPD) pattern having peaks at 6.9, 8.2, 15.7, and 18.8 degrees 2θ (±0.1 degrees 2θ), wherein the XRPD is made using CuK$_{\alpha 1}$ radiation. In some embodiments, the solid Form I of Compound I can be characterized by an X-ray powder diffraction (XRPD) pattern having peaks at 6.9, 8.2, 12.5, 14.8, 15.7, and 18.8 degrees 2θ (±0.1 degrees 2θ), wherein the XRPD is made using CuK$_{\alpha 1}$ radiation. In some embodiments, the solid Form I of Compound I can be characterized by an X-ray powder diffraction (XRPD) pattern having peaks at 6.9, 8.2, 12.5, 14.8, 15.7, 18.8, and 21.1 degrees 2θ (±0.1 degrees 2θ), wherein the XRPD is made using CuK$_{\alpha 1}$ radiation. In some embodiments, the solid Form I of Compound I can be characterized by an X-ray powder diffraction (XRPD) pattern having peaks at 6.9, 8.2, 12.5, 14.8, 15.7, 18.8, 20.6, and 21.1 degrees 2θ (±0.1 degrees 2θ), wherein the XRPD is made using CuK$_{\alpha 1}$ radiation. In some embodiments, the solid Form I of Compound I can be characterized by an X-ray powder diffraction (XRPD) pattern having peaks at 6.9, 8.2, 12.5, 14.8, 15.7, 18.8, 20.6, 21.1, and 27.7 degrees 2θ (±0.1 degrees 2θ), wherein the XRPD is made using CuK$_{\alpha 1}$ radiation.

In some embodiments, the solid Form I of Compound I can be characterized by an XRPD pattern having peaks at 6.9, 8.0, 8.2, 12.5, 12.7, 14.8, 15.0, 15.7, 16.8, 18.1, 18.8, 19.2, 20.6, 21.1, 21.8, 24.9, 27.1, and 27.7 degrees 2θ (±0.1 degrees 2θ), wherein the XRPD is made using CuKα1 radiation. In some embodiments, the solid Form I of Compound I can be characterized by an XRPD pattern according to the peaks in Table 1 below:

TABLE 1

XRPD Peak List for Sample of Form I of Compound I

| 2θ (degrees) | Intensity (counts) | Intensity (percent) |
| --- | --- | --- |
| 6.9 | 3091 | 100 |
| 8.0 | 747 | 24 |
| 8.2 | 1734 | 56 |
| 12.5 | 929 | 30 |
| 12.7 | 882 | 29 |
| 14.8 | 1420 | 46 |
| 15.0 | 1057 | 34 |
| 15.7 | 1649 | 53 |
| 16.8 | 658 | 21 |
| 18.1 | 820 | 27 |
| 18.8 | 1536 | 50 |
| 19.2 | 1028 | 33 |
| 20.6 | 849 | 27 |
| 21.1 | 1319 | 43 |
| 21.8 | 762 | 25 |
| 24.9 | 717 | 23 |
| 27.1 | 917 | 30 |
| 27.7 | 922 | 30 |

In some embodiments, the solid Form I of Compound I can be characterized by the XRPD pattern substantially in accordance with that of FIG. 1. In some embodiments, the solid Form I of Compound I can be substantially free of other solid forms of Compound I. In some embodiments, the solid Form I of Compound I can be substantially free of Form II and Form III.

Figure 2:
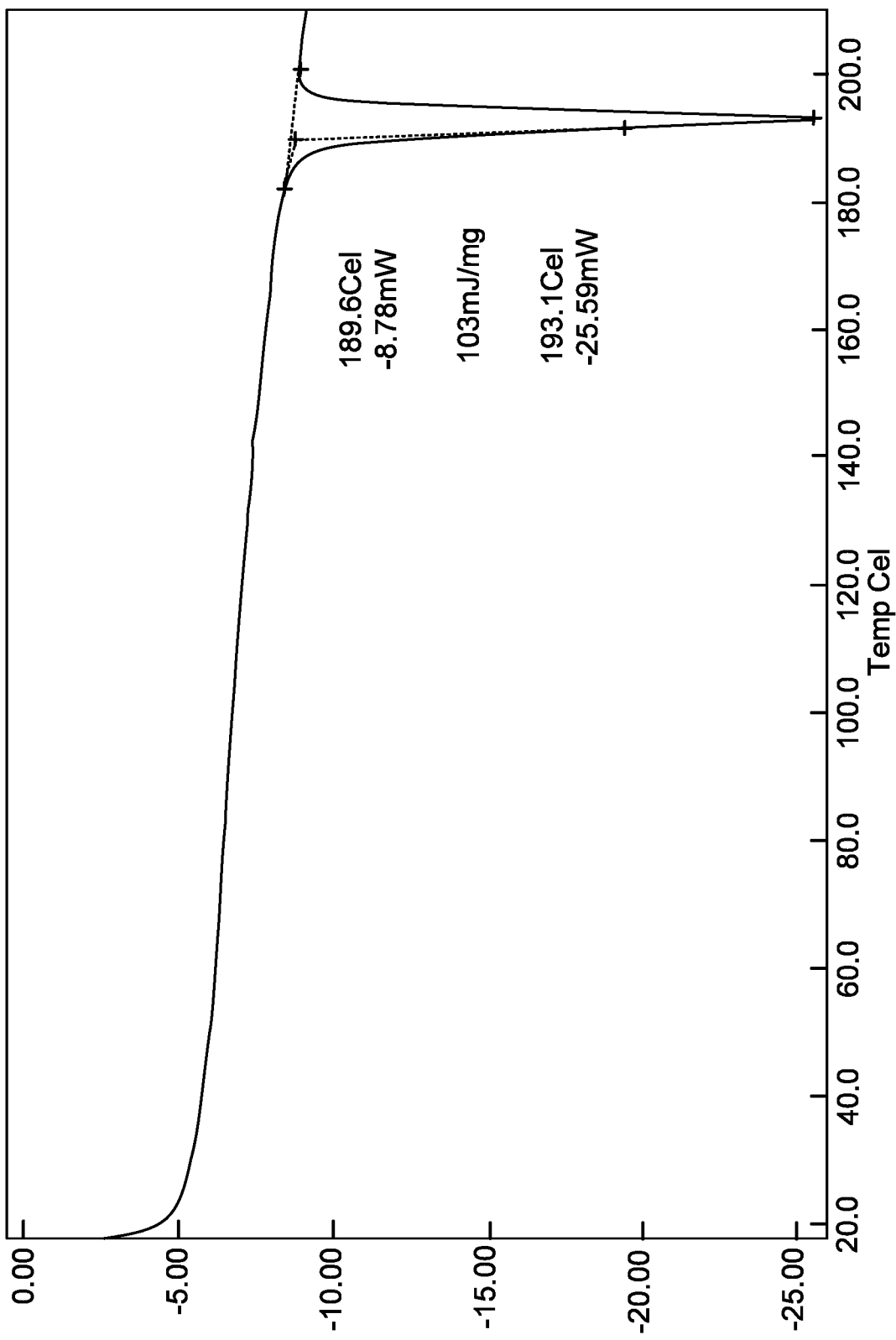
FIG. 2 shows a differential scanning calorimetry (DSC) plot of Compound I Form I showing an endotherm at about 193° C.
Figure 3:
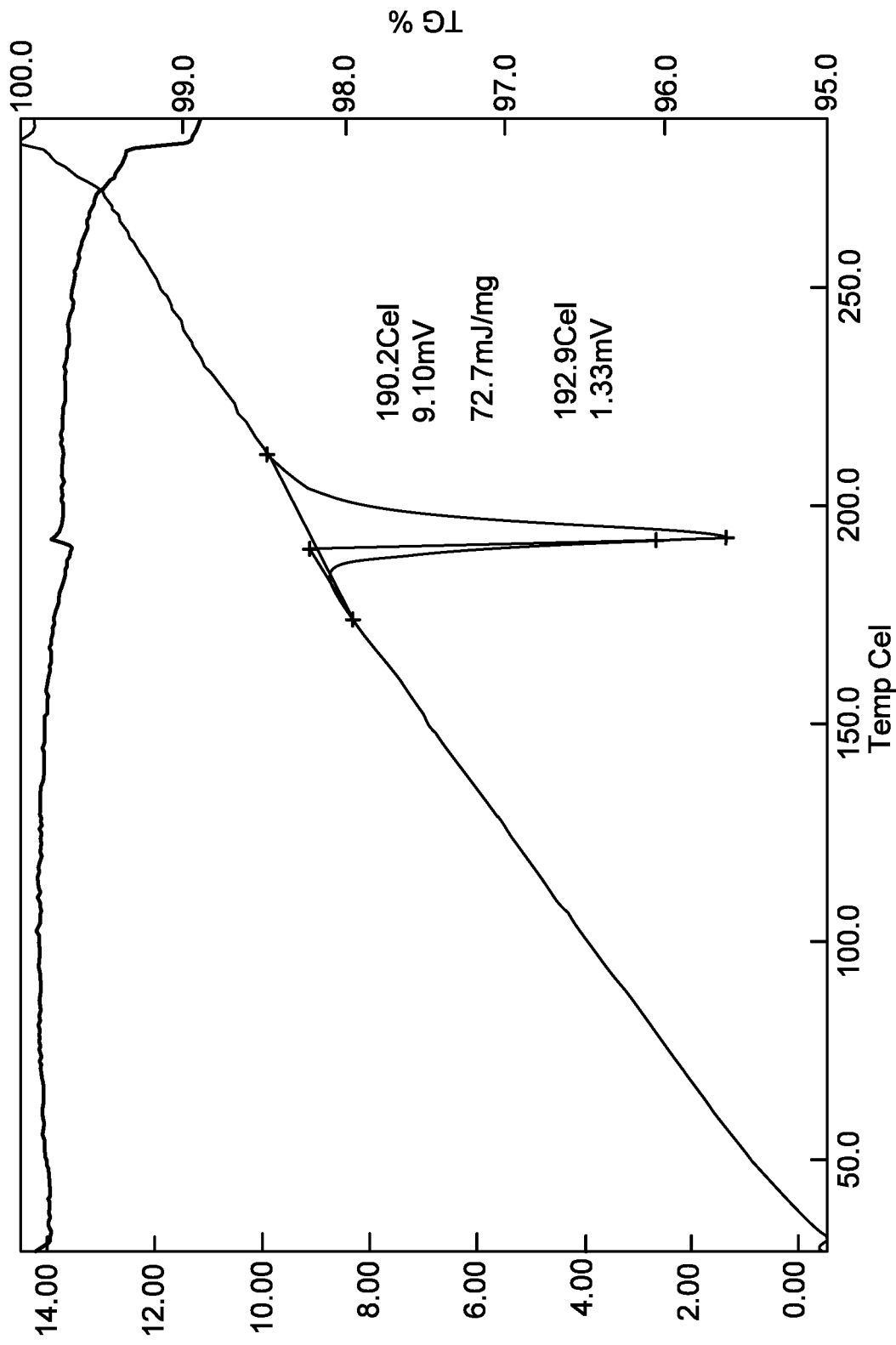
FIG. 3 shows a thermogravimetric analysis (TGA) of Compound I Form I.

Form I of Compound I can be characterized by a differential scanning calorimetry (DSC) plot having an endotherm at about 193° C. In some embodiments, the solid Form I of Compound I can be characterized by the DSC pattern substantially in accordance with that of FIG. 2.

Form I of Compound I can be characterized by one or more characteristics of the single crystal X-ray diffraction data shown in the following Table 2.

TABLE 2

Single crystal X-ray diffraction data for Form I of Compound I

| X-ray parameter | Form I |
| --- | --- |
| Crystal system | Monoclinic |
| Space group | P 1 21/c 1 |
| a | 15.1880(7) Å |
| b | 20.9125(11) Å |
| c | 7.5242(4) Å |
| α | 90° |
| β | 90.7720(10)° |
| γ | 90° |
| Z | 4 |
| Volume | 2389.6(2) Å$^3$ |
| Density (calculated) | 1.185 g/cm$^3$ |

Form II

Form II of Compound I can be characterized by an X-ray powder diffraction (XRPD) pattern having one or more, e.g., two, three, four, five, or more, peaks at 7.1, 7.8, 8.2, 8.7, 12.4, 13.9, 14.9, 15.3, 15.6, 17.5, 18.3, 19.3, 19.8, 20.2, 21.4, 22.2, 25.0, 25.6, 26.4, or 27.1 degrees 2θ (±0.1 degrees 2θ), wherein the XRPD is made using CuK$_{\alpha 1}$ radiation. In some embodiments, the solid Form II of Compound I can be characterized by an X-ray powder diffraction pattern having two or more peaks at 7.1, 7.8, 8.2, 8.7, 12.4, 13.9, 14.9, 15.3, 15.6, 17.5, 18.3, 19.3, 19.8, 20.2, 21.4, 22.2, 25.0, 25.6, 26.4, or 27.1 degrees 2θ (±0.1 degrees 2θ), wherein the XRPD is made using CuK$_{\alpha 1}$ radiation. In some embodiments, the solid Form II of Compound I can be characterized by an X-ray powder diffraction pattern having three or more peaks at 7.1, 7.8, 8.2, 8.7, 12.4, 13.9, 14.9, 15.3, 15.6, 17.5, 18.3, 19.3, 19.8, 20.2, 21.4, 22.2, 25.0, 25.6, 26.4, or 27.1 degrees 2θ (±0.1 degrees 2θ), wherein the XRPD is made using CuK$_{α1}$ radiation. In some embodiments, the solid Form II of Compound I can be characterized by an X-ray powder diffraction pattern having four or more peaks at 7.1, 7.8, 8.2, 8.7, 12.4, 13.9, 14.9, 15.3, 15.6, 17.5, 18.3, 19.3, 19.8, 20.2, 21.4, 22.2, 25.0, 25.6, 26.4, or 27.1 degrees 2θ (±0.1 degrees 2θ), wherein the XRPD is made using CuK$_{α1}$ radiation. In some embodiments, the solid Form II of Compound I can be characterized by an X-ray powder diffraction pattern having five or more peaks at 7.1, 7.8, 8.2, 8.7, 12.4, 13.9, 14.9, 15.3, 15.6, 17.5, 18.3, 19.3, 19.8, 20.2, 21.4, 22.2, 25.0, 25.6, 26.4, or 27.1 degrees 2θ (±0.1 degrees 2θ), wherein the XRPD is made using CuK$_{α1}$ radiation.

In some embodiments, the solid Form II of Compound I can be characterized by an X-ray powder diffraction pattern having six or more peaks at 7.1, 7.8, 8.2, 8.7, 12.4, 13.9, 14.9, 15.3, 15.6, 17.5, 18.3, 19.3, 19.8, 20.2, 21.4, 22.2, 25.0, 25.6, 26.4, or 27.1 degrees 2θ (±0.1 degrees 2θ), wherein the XRPD is made using CuK$_{α1}$ radiation. In some embodiments, the solid Form II of Compound I can be characterized by an X-ray powder diffraction pattern having seven or more peaks at 7.1, 7.8, 8.2, 8.7, 12.4, 13.9, 14.9, 15.3, 15.6, 17.5, 18.3, 19.3, 19.8, 20.2, 21.4, 22.2, 25.0, 25.6, 26.4, or 27.1 degrees 2θ (±0.1 degrees 2θ), wherein the XRPD is made using CuK$_{α1}$ radiation. In some embodiments, the solid Form II of Compound I can be characterized by an X-ray powder diffraction pattern having eight or more peaks at 7.1, 7.8, 8.2, 8.7, 12.4, 13.9, 14.9, 15.3, 15.6, 17.5, 18.3, 19.3, 19.8, 20.2, 21.4, 22.2, 25.0, 25.6, 26.4, or 27.1 degrees 2θ (±0.1 degrees 2θ), wherein the XRPD is made using CuK$_{α1}$ radiation. In some embodiments, the solid Form II of Compound I can be characterized by an X-ray powder diffraction pattern having nine or more peaks at 7.1, 7.8, 8.2, 8.7, 12.4, 13.9, 14.9, 15.3, 15.6, 17.5, 18.3, 19.3, 19.8, 20.2, 21.4, 22.2, 25.0, 25.6, 26.4, or 27.1 degrees 2θ (±0.1 degrees 2θ), wherein the XRPD is made using CuK$_{α1}$ radiation. In some embodiments, the solid Form II of Compound I can be characterized by an X-ray powder diffraction pattern having ten or more peaks at 7.1, 7.8, 8.2, 8.7, 12.4, 13.9, 14.9, 15.3, 15.6, 17.5, 18.3, 19.3, 19.8, 20.2, 21.4, 22.2, 25.0, 25.6, 26.4, or 27.1 degrees 2θ (±0.1 degrees 2θ), wherein the XRPD is made using CuK$_{α1}$ radiation.

In some embodiments, the solid Form II of Compound I can be characterized by an XRPD pattern having peaks at 7.1, 7.8, and 18.3 degrees 2θ (±0.1 degrees 2θ), wherein the XRPD is made using CuK$_{α1}$ radiation. In some embodiments, the solid Form II of Compound I can be characterized by an X-ray powder diffraction (XRPD) pattern further comprising one or more peaks at 8.7, 13.9, 14.9, 15.6, or 22.2 degrees 2θ (±0.1 degrees 2θ), wherein the XRPD is made using CuK$_{α1}$ radiation. In some embodiments, the solid Form II of Compound I can be characterized by an X-ray powder diffraction (XRPD) pattern further comprising two or more peaks at 8.7, 13.9, 14.9, 15.6, or 22.2 degrees 2θ (±0.1 degrees 2θ), wherein the XRPD is made using CuK$_{α1}$ radiation. In some embodiments, the solid Form II of Compound I can be characterized by an X-ray powder diffraction (XRPD) pattern further comprising three or more peaks at 8.7, 13.9, 14.9, 15.6, or 22.2 degrees 2θ (±0.1 degrees 2θ), wherein the XRPD is made using CuK$_{α1}$ radiation. In some embodiments, the solid Form II of Compound I can be characterized by an X-ray powder diffraction (XRPD) pattern further comprising four or more peaks at 8.7, 13.9, 14.9, 15.6, or 22.2 degrees 2θ (±0.1 degrees 2θ), wherein the XRPD is made using CuK$_{α1}$ radiation.

In some embodiments, the solid Form II of Compound I can be characterized by an XRPD pattern having peaks at 7.1, 7.8, 14.9, and 18.3 degrees 2θ (±0.1 degrees 2θ), wherein the XRPD is made using CuK$_{α1}$ radiation. In some embodiments, the solid Form II of Compound I can be characterized by an XRPD pattern having peaks at 7.1, 7.8, 8.7, 14.9, and 18.3 degrees 2θ (±0.1 degrees 2θ), wherein the XRPD is made using CuK$_{α1}$ radiation. In some embodiments, the solid Form II of Compound I can be characterized by an XRPD pattern having peaks at 7.1, 7.8, 13.9, 14.9, and 18.3 degrees 2θ (±0.1 degrees 2θ), wherein the XRPD is made using CuK$_{α1}$ radiation. In some embodiments, the solid Form II of Compound I can be characterized by an XRPD pattern having peaks at 7.1, 7.8, 13.9, 14.9, 15.6, and 18.3 degrees 2θ (±0.1 degrees 2θ), wherein the XRPD is made using CuK$_{α1}$ radiation.

In some embodiments, the solid Form II of Compound I can be characterized by an X-ray powder diffraction pattern having peaks at 7.1, 7.8, 8.2, 8.7, 12.4, 13.9, 14.9, 15.3, 15.6, 17.5, 18.3, 19.3, 19.8, 20.2, 21.4, 22.2, 25.0, 25.6, 26.4, or 27.1 degrees 2θ (±0.1 degrees 2θ), wherein the XRPD is made using CuK$_{α1}$ radiation. In some embodiments, the solid Form II of Compound I can be characterized by a peak list according to Table 3 below:

TABLE 3

XRPD Peak List for Sample of Form II of Compound I

| 2θ (degrees) | Intensity (counts) | Intensity (percent) |
|---|---|---|
| 7.1 | 5909 | 90 |
| 7.8 | 6600 | 100 |
| 8.2 | 1936 | 29 |
| 8.7 | 4350 | 66 |
| 12.4 | 1463 | 22 |
| 13.9 | 3141 | 48 |
| 14.9 | 4991 | 76 |
| 15.3 | 2231 | 34 |
| 15.6 | 2841 | 43 |
| 17.5 | 2418 | 37 |
| 18.3 | 5129 | 78 |
| 19.3 | 1323 | 20 |
| 19.8 | 1081 | 16 |
| 20.2 | 2000 | 30 |
| 21.4 | 1102 | 17 |
| 22.2 | 2476 | 38 |
| 25.0 | 1818 | 28 |
| 25.6 | 1262 | 19 |
| 26.4 | 1428 | 22 |
| 27.1 | 1507 | 23 |

Figure 5:
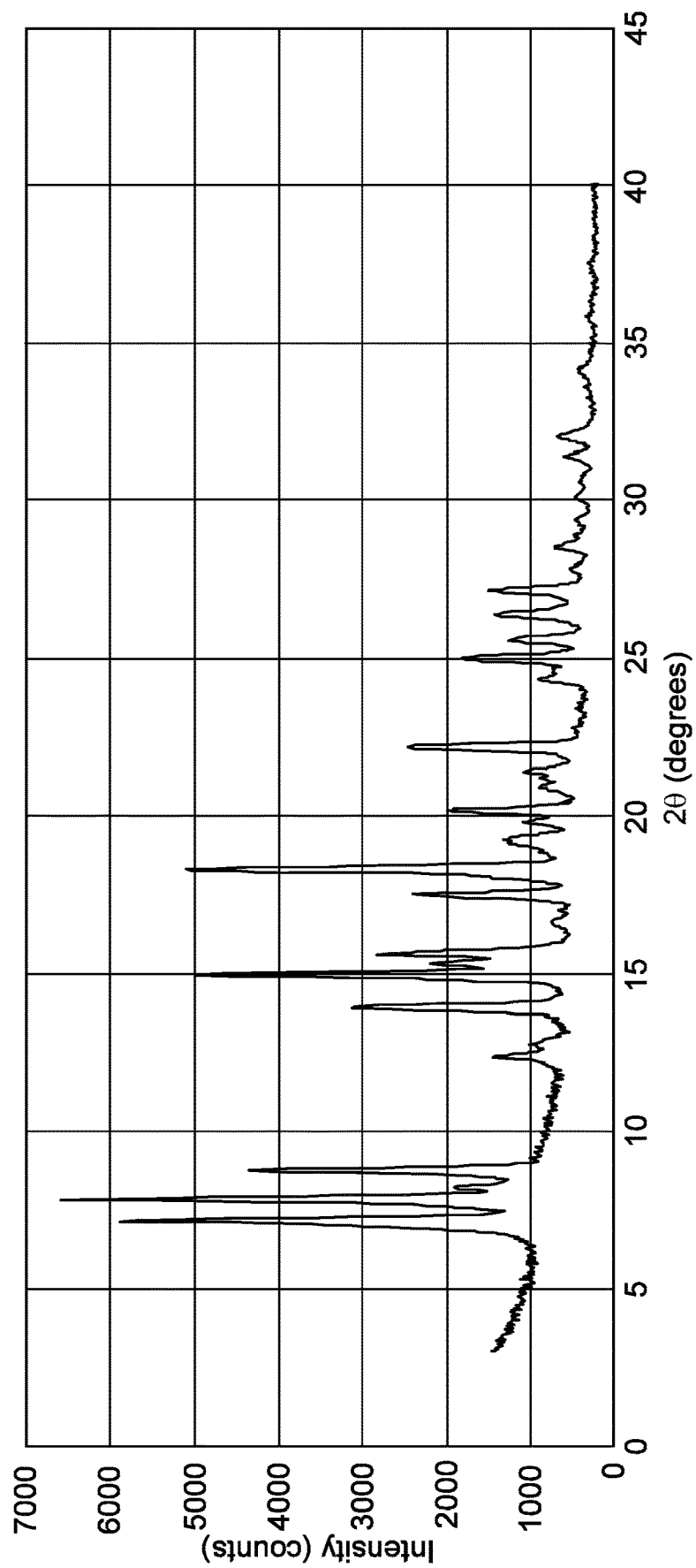
FIG. 5 shows an X-ray powder diffraction (XRPD) pattern of Compound I Form II.

In some embodiments, the solid Form II of Compound I can be characterized by the XRPD pattern substantially in accordance with that of FIG. 5. In some embodiments, the solid Form II of Compound I can be substantially free of other solid forms of Compound I. In some embodiments, the solid Form II of Compound I can be substantially free of Form I and Form III.

Form II of Compound I can be characterized by a differential scanning calorimetry (DSC) plot having an endotherm at about 190° C. In some embodiments, the solid Form I of Compound I can be characterized by the DSC pattern substantially in accordance with that of FIG. 6.

In some embodiments, the solid Form II of Compound I can be characterized by the XRPD pattern substantially in accordance with that of FIG. 5 and a DSC plot having an endotherm at about 190° C.

Form III

Form III of Compound I can be characterized by an X-ray powder diffraction (XRPD) pattern having one or more, e.g., two, three, four, five, or more, peaks at 10.8, 12.2, 12.6, 13.7, 15.2, 15.3, 16.5, 17.2, 17.8, 18.1, 18.4, 19.3, 19.5, 20.7, 21.3, 23.1, 23.9, 24.7, 25.3, or 28.4 degrees 2θ (±0.1 degrees 2θ), wherein the XRPD is made using CuK$_{\alpha1}$ radiation. In some embodiments, the solid Form III of Compound I can be characterized by an X-ray powder diffraction pattern having two or more peaks at 10.8, 12.2, 12.6, 13.7, 15.2, 15.3, 16.5, 17.2, 17.8, 18.1, 18.4, 19.3, 19.5, 20.7, 21.3, 23.1, 23.9, 24.7, 25.3, or 28.4 degrees 2θ (±0.1 degrees 2θ), wherein the XRPD is made using CuK$_{\alpha1}$ radiation. In some embodiments, the solid Form III of Compound I can be characterized by an X-ray powder diffraction pattern having three or more peaks at 10.8, 12.2, 12.6, 13.7, 15.2, 15.3, 16.5, 17.2, 17.8, 18.1, 18.4, 19.3, 19.5, 20.7, 21.3, 23.1, 23.9, 24.7, 25.3, or 28.4 degrees 2θ (±0.1 degrees 2θ), wherein the XRPD is made using CuK$_{\alpha1}$ radiation. In some embodiments, the solid Form III of Compound I can be characterized by an X-ray powder diffraction pattern having four or more peaks at 10.8, 12.2, 12.6, 13.7, 15.2, 15.3, 16.5, 17.2, 17.8, 18.1, 18.4, 19.3, 19.5, 20.7, 21.3, 23.1, 23.9, 24.7, 25.3, or 28.4 degrees 2θ (±0.1 degrees 2θ), wherein the XRPD is made using CuK$_{\alpha1}$ radiation. In some embodiments, the solid Form III of Compound I can be characterized by an X-ray powder diffraction pattern having five or more peaks at 10.8, 12.2, 12.6, 13.7, 15.2, 15.3, 16.5, 17.2, 17.8, 18.1, 18.4, 19.3, 19.5, 20.7, 21.3, 23.1, 23.9, 24.7, 25.3, or 28.4 degrees 2θ (±0.1 degrees 2θ), wherein the XRPD is made using CuK$_{\alpha1}$ radiation.

In some embodiments, the solid Form III of Compound I can be characterized by an X-ray powder diffraction pattern having six or more peaks at 10.8, 12.2, 12.6, 13.7, 15.2, 15.3, 16.5, 17.2, 17.8, 18.1, 18.4, 19.3, 19.5, 20.7, 21.3, 23.1, 23.9, 24.7, 25.3, or 28.4 degrees 2θ (±0.1 degrees 2θ), wherein the XRPD is made using CuK$_{\alpha1}$ radiation. In some embodiments, the solid Form III of Compound I can be characterized by an X-ray powder diffraction pattern having seven or more peaks at 10.8, 12.2, 12.6, 13.7, 15.2, 15.3, 16.5, 17.2, 17.8, 18.1, 18.4, 19.3, 19.5, 20.7, 21.3, 23.1, 23.9, 24.7, 25.3, or 28.4 degrees 2θ (±0.1 degrees 2θ), wherein the XRPD is made using CuK$_{\alpha1}$ radiation. In some embodiments, the solid Form III of Compound I can be characterized by an X-ray powder diffraction pattern having eight or more peaks at 10.8, 12.2, 12.6, 13.7, 15.2, 15.3, 16.5, 17.2, 17.8, 18.1, 18.4, 19.3, 19.5, 20.7, 21.3, 23.1, 23.9, 24.7, 25.3, or 28.4 degrees 2θ (±0.1 degrees 2θ), wherein the XRPD is made using CuK$_{\alpha1}$ radiation. In some embodiments, the solid Form III of Compound I can be characterized by an X-ray powder diffraction pattern having nine or more peaks at 10.8, 12.2, 12.6, 13.7, 15.2, 15.3, 16.5, 17.2, 17.8, 18.1, 18.4, 19.3, 19.5, 20.7, 21.3, 23.1, 23.9, 24.7, 25.3, or 28.4 degrees 2θ (±0.1 degrees 2θ), wherein the XRPD is made using CuK$_{\alpha1}$ radiation. In some embodiments, the solid Form III of Compound I can be characterized by an X-ray powder diffraction pattern having ten or more peaks at 10.8, 12.2, 12.6, 13.7, 15.2, 15.3, 16.5, 17.2, 17.8, 18.1, 18.4, 19.3, 19.5, 20.7, 21.3, 23.1, 23.9, 24.7, 25.3, or 28.4 degrees 2θ (±0.1 degrees 2θ), wherein the XRPD is made using CuK$_{\alpha1}$ radiation.

In some embodiments, the solid Form III of Compound I can be characterized by an XRPD pattern having peaks at 12.2, 20.7, and 21.3 degrees 2θ (±0.1 degrees 2θ), wherein the XRPD is made using CuK$_{\alpha1}$ radiation. In some embodiments, the solid Form III of Compound I can be characterized by an X-ray powder diffraction (XRPD) pattern further comprising one or more peaks at 10.8, 12.6, 17.2, or 19.3 degrees 2θ (±0.1 degrees 2θ), wherein the XRPD is made using CuK$_{\alpha1}$ radiation. In some embodiments, the solid Form III of Compound I can be characterized by an X-ray powder diffraction (XRPD) pattern further comprising two or more peaks at 10.8, 12.6, 17.2, or 19.3 degrees 2θ (±0.1 degrees 2θ), wherein the XRPD is made using CuK$_{\alpha1}$ radiation. In some embodiments, the solid Form III of Compound I can be characterized by an X-ray powder diffraction (XRPD) pattern further comprising three or more peaks at 10.8, 12.6, 17.2, or 19.3 degrees 2θ (±0.1 degrees 2θ), wherein the XRPD is made using CuK$_{\alpha1}$ radiation.

In some embodiments, the solid Form III of Compound I can be characterized by an XRPD pattern having peaks at 12.2, 12.6, 20.7, and 21.3 degrees 2θ (±0.1 degrees 2θ), wherein the XRPD is made using CuK$_{\alpha1}$ radiation. In some embodiments, the solid Form III of Compound I can be characterized by an XRPD pattern having peaks at 12.2, 17.2, 20.7, and 21.3 degrees 2θ (±0.1 degrees 2θ), wherein the XRPD is made using CuK$_{\alpha1}$ radiation. In some embodiments, the solid Form III of Compound I can be characterized by an XRPD pattern having peaks at 12.2, 12.6, 17.2, 20.7, and 21.3 degrees 2θ (±0.1 degrees 2θ), wherein the XRPD is made using CuK$_{\alpha1}$ radiation. In some embodiments, the solid Form III of Compound I can be characterized by an XRPD pattern having peaks at 10.8, 12.2, 12.6, 17.2, 20.7, and 21.3 degrees 2θ (±0.1 degrees 2θ), wherein the XRPD is made using CuK$_{\alpha1}$ radiation. In some embodiments, the solid Form III of Compound I can be characterized by an XRPD pattern having peaks at 10.8, 12.2, 12.6, 17.2, 19.3, 20.7, and 21.3 degrees 2θ (±0.1 degrees 2θ), wherein the XRPD is made using CuK$_{\alpha1}$ radiation. In some embodiments, the solid Form III of Compound I can be characterized by an XRPD pattern having peaks at 10.8, 12.2, 12.6, 17.2, 19.3, 20.7, 21.3, and 23.9 degrees 2θ (±0.1 degrees 2θ), wherein the XRPD is made using CuK$_{\alpha1}$ radiation. In some embodiments, the solid Form III of Compound I can be characterized by an XRPD pattern having peaks at 10.8, 12.2, 12.6, 17.2, 19.3, 20.7, 21.3, 23.9, and 24.7 degrees 2θ (±0.1 degrees 2θ), wherein the XRPD is made using CuK$_{\alpha1}$ radiation.

In some embodiments, the solid Form III of Compound I can be characterized by an X-ray powder diffraction pattern having peaks at 10.8, 12.2, 12.6, 13.7, 15.2, 15.3, 16.5, 17.2, 17.8, 18.1, 18.4, 19.3, 19.5, 20.7, 21.3, 23.1, 23.9, 24.7, 25.3, and 28.4 degrees 2θ (±0.1 degrees 2θ), wherein the XRPD is made using CuK$_{\alpha1}$ radiation. In some embodiments, the solid Form III of Compound I can be characterized by a peak list according to Table 4 below:

TABLE 4

XRPD Peak List for Sample of Form III of Compound I

| 2θ (degrees) | Intensity (counts) | Intensity (percent) |
| --- | --- | --- |
| 10.8 | 602 | 50 |
| 12.2 | 797 | 67 |
| 12.6 | 649 | 54 |
| 13.7 | 214 | 18 |
| 15.2 | 410 | 34 |
| 15.3 | 376 | 31 |
| 16.5 | 222 | 19 |
| 17.2 | 644 | 54 |
| 17.8 | 209 | 17 |
| 18.1 | 282 | 24 |
| 18.4 | 312 | 26 |
| 19.3 | 524 | 44 |

TABLE 4-continued

XRPD Peak List for Sample of Form III of Compound I

| 2θ (degrees) | Intensity (counts) | Intensity (percent) |
|---|---|---|
| 19.5 | 286 | 24 |
| 20.7 | 651 | 54 |
| 21.3 | 1195 | 100 |
| 23.1 | 372 | 31 |
| 23.9 | 480 | 40 |
| 24.7 | 449 | 38 |
| 25.3 | 205 | 17 |
| 28.4 | 284 | 24 |

Figure 7:
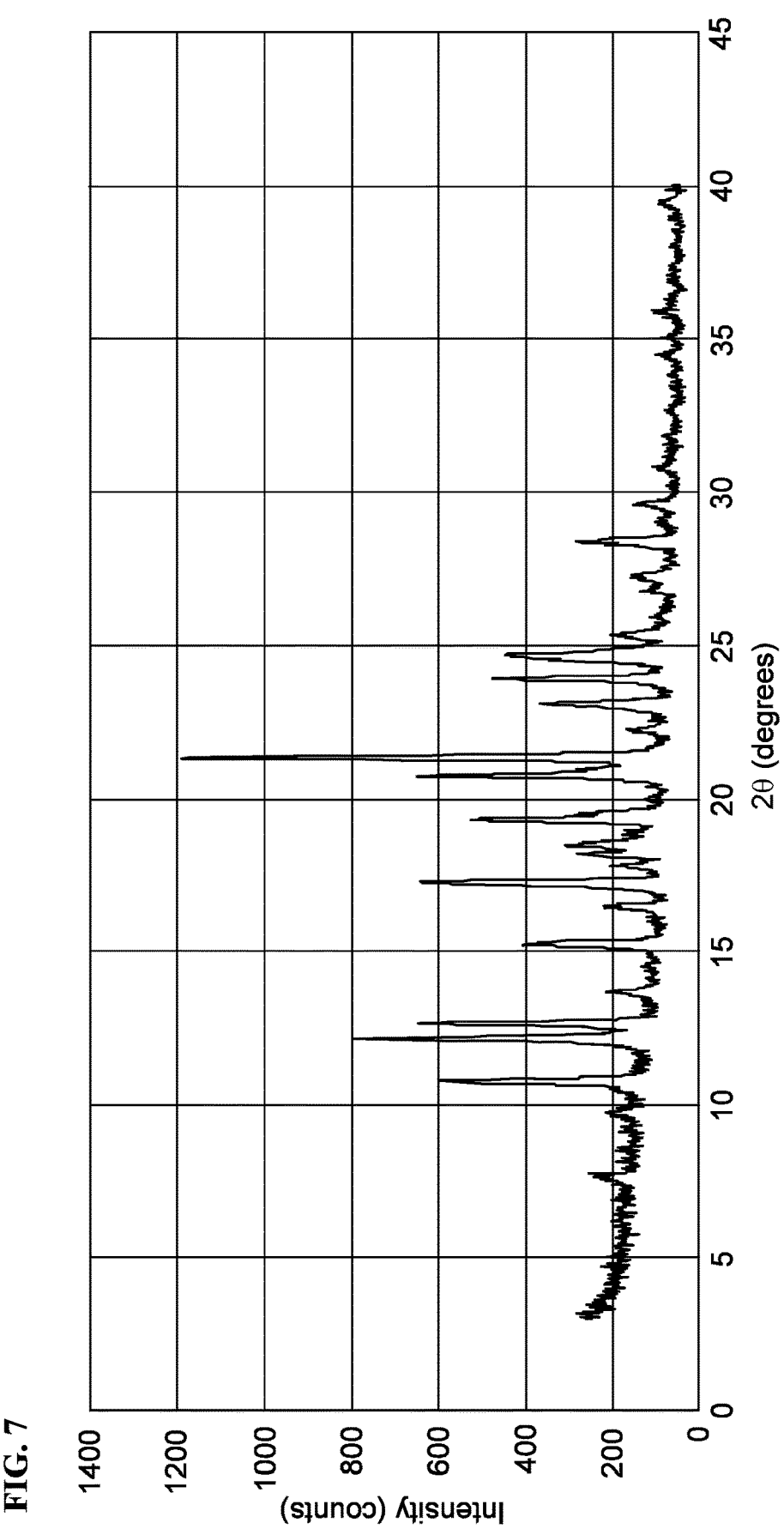
FIG. 7 shows X-ray powder diffraction (XRPD) patterns of Compound I Form III.

In some embodiments, the solid Form III of Compound I can be characterized by the XRPD pattern substantially in accordance with one selected from those shown in FIG. 7. In some embodiments, the solid Form III of Compound I can be substantially free of other solid forms of Compound I. In some embodiments, the solid Form III of Compound I can be substantially free of Form I and Form II.

Form III of Compound I can be characterized by a differential scanning calorimetry (DSC) plot having one or more endotherms at about 178° C. and about 193° C. In some embodiments, the solid Form III of Compound I can be characterized by the DSC pattern having an endotherm at about 178° C. In some embodiments, the solid Form III of Compound I can be characterized by the DSC pattern substantially in accordance with that of FIG. 8.

In some embodiments, the solid Form III of Compound I can be characterized by the XRPD pattern substantially in accordance with that of FIG. 7 and a DSC plot having one or more endotherms at about 178° C. and about 193° C.

Methods of Making

The solid forms of Compound I provided herein can be prepared by methods as described below and in the Examples.

Suitability of Starting Material

In general, the morphology of the starting Compound I material is unimportant with respect to the successful recovery of a solid form of Compound I, although the kinetics of initial dissolution may be affected. For example, amorphous material obtained via lyophilization may be used to obtain the desired solid form. Alternatively, one solid form of Compound I may be used to obtain another solid form of Compound I, e.g., a less stable solid form may be used to obtain a more stable form.

Single Solvents and Binary Solvent Mixtures

The solvent can be any solvent suitable to form a solution. Typically the solvent can be a polar solvent, which in some embodiments is a protic solvent. Other suitable solvents include non-polar solvents. A variety of solvents can be used to generate the desired solid form of Compound I, either through use of a single solvent or a binary solvent mixture. In the case of a single solvent the starting Compound I material is dissolved by heating in a solvent capable of forming a reasonably concentrated solution, followed by cooling to initiate formation of the desired crystalline form. Suitable single solvents include but are not limited to ethers, e.g., 1,4-dioxane, diethyl ether and methyl tert-butyl ether; alkanoates such as ethyl acetate, propyl acetate, isopropyl acetate, and butyl acetate; ethylene glycol and polyethylene glycol such as PEG400; ketones such as $C_3$-$C_5$ ketones, e.g., methyl ethyl ketone and acetone; alcohols such as $C_1$-$C_3$ alcohols, e.g., methanol, isopropanol and ethanol; aromatics such as benzene and toluene; halogenated solvents such as methylene chloride, chloroform and carbon tetrachloride; dimethylsulfoxide (DMSO); and dimethylformamide (DMF).

Slow evaporation of a saturated solution of material in an appropriate solvent is also effective in obtaining crystalline material. Suitable solvents include but are not limited to ethers, e.g., 1,4-dioxane, diethyl ether and methyl tert-butyl ether; alkanoates such as ethyl acetate, propyl acetate, isopropyl acetate, and butyl acetate; ketones such as $C_3$-$C_5$ ketones, e.g., methyl ethyl ketone and acetone; and alcohols such as $C_1$-$C_3$ alcohols, e.g., methanol, isopropanol and ethanol.

In the case of a binary solvent mixture, the material is first dissolved in a solvent capable of forming a reasonably concentrated solution as outlined above, and, while the solution is still hot, addition of a less polar solvent, i.e., the anti-solvent, in which the material is not readily soluble to initiate crystallization of the desired material. In a selected example, the material is dissolved in acetone with heating and water added to initiate formation of the desired crystalline form. Suitable anti-solvents include but are not limited to alkanes such as $C_5$-$C_7$ alkanes, e.g., n-pentane and n-heptane; ethers, e.g., 1,4-dioxane, diethyl ether and methyl tert-butyl ether; alkanoates, e.g., isobutyl acetate; methyl ethyl ketone; and water.

Solvent/Anti-Solvent Ratio

In the case of a binary solvent mixture, the ratio of solvent to precipitating solvent, i.e., the anti-solvent added to form a supersaturated solution of Compound I, does not greatly affect the formation of the solid form of Compound I, provided sufficient anti-solvent is added to initiate crystallization of the product. The solvent to anti-solvent ratio can affect the percent recovery of the crystalline form relative to the starting amount of Compound I.

Solvent/Compound Ratio

The ratio or concentration of Compound I relative to solvent can be variable depending on the solvent or solvent mixture used. Typical concentrations can range from 200 mg/mL to 10 mg/mL with the limiting factor at the higher end being the solubility of the material or the ease of recovery of the material once crystallization has occurred. For example, approximately 70 mg of Compound I can be dissolved in 1 mL of acetone with subsequent addition of water to afford the crystalline form.

Temperature

The methods of preparing crystalline forms of Compound I can be performed under any suitable reaction conditions. For example, the methods of preparing the crystalline forms of Compound I can be performed at any suitable temperature, such as, but not limited to, below room temperature, at room temperature, or above room temperature. In general, the temperature used in the methods of making described herein can range from about 20° C. to the reflux temperature of the solvent. Typical temperatures range from about 50° C. to about 80° C. Once a solution has been obtained, and, if required, a precipitating solvent, i.e., an anti-solvent, added, the mixture is cooled to room temperature. The rate of cooling can affect the size, shape, and quality of the crystals in the isolated solid form of Compound I.

Rate of Crystallization

Several factors significantly impact a rate of crystallization. These include, but are not limited to: rate of anti-solvent addition, rate of mixture cooling, and presence of nucleation sites such as dust, seed crystals, or defects on the glass surface. Variations in these parameters can affect the size, shape, and quality of the crystals in the isolated solid form of Compound I.

The methods of preparing crystalline forms of Compound I can be performed for any suitable time. For example, the time can be for minutes, hours or days. In some embodiments, the time can be several hours, such as overnight. The methods of preparing crystalline forms of Compound I can be also be performed at any suitable pressure. For example, the pressure can be below atmospheric pressure, at about atmospheric pressure, or above atmospheric pressure.

Isolation of the Solid Form of Compound I

Several methods for isolation of the desired solid form, e.g., a crystalline form, from the supernatant can be used including filtration, decantation, and solvent evaporation. In general, the crystalline form was obtained by collecting any formed solid by vacuum filtration, followed by air-drying and subsequent exposure to high vacuum to remove any residual solvent.

Form I

In some embodiments, the present invention provides a method of preparing Form I of Compound I of the present invention, including forming a mixture of Compound I of the present invention, and a solvent, under conditions suitable to prepare Form I. Any suitable solvent can be used in the method of preparing Compound I Form I. In some embodiments, the solvent can be at least one of toluene, ethanol, isopropanol, methyl ethyl ketone (i.e., 2-butanone), acetone, acetonitrile, isobutyl acetate, ethyl acetate, DMSO, or dichloromethane. In some embodiments, the solvent can be at least one of acetone, ethanol, isopropanol, or dichloromethane. In some embodiments, the solvent can include one of acetone, ethanol, or isopropanol. In some embodiments, the solvent can be at least one of acetone, ethanol, or isopropanol, in combination with water. In some embodiments, the solvent can be acetone and water.

In some embodiments, the present invention provides a method of preparing a crystalline Form I of Compound I by forming a mixture of Compound I, and a solvent including a $C_3$-$C_5$ ketone, dichloromethane, or toluene, under conditions suitable to prepare Form I. The $C_3$-$C_5$ ketone can be acetone, methyl ethyl ketone, or 3-pentanone. In some embodiments, the solvent includes one of acetone and methyl ethyl ketone.

Any suitable ratio of the acetone and water can be used. For example, if the material is dissolved in acetone and water is added as an anti-solvent, the acetone to water ratio can vary from about 9:1 to about 1:9 (volume:volume), e.g., from about 3:1 to about 1:5 or from about 1:1 to about 1:6. In some embodiments, the acetone to water ratio (volume:volume) is about 9:1, 8:1, 7:1, 6:1, 5:1, 4:1, 3:1, 2:1, 1:1, 1:2, 1:3, 1:4, 1:5, 1:6, 1:7, 1:8, or about 1:9. In some embodiments, the acetone to water ratio (volume:volume) is about 1:3 or about 1:4.

Form II

The present invention also provides methods for preparing Compound I Form II. In some embodiments, the present invention provides a method of preparing a Form II of Compound I by forming a mixture of Compound I and acetonitrile, under conditions suitable to prepare Form II. In some embodiments, the method of preparing a Form II of Compound I comprises forming a mixture of Compound I, acetonitrile, and water.

Any suitable ratio of the acetonitrile and water can be used. For example, if the Compound I is dissolved in acetonitrile and water is added as an anti-solvent, the acetone to water ratio can vary from about 9:1 to about 1:9 (volume:volume), e.g., from about 3:1 to about 1:5 or from about 1:1 to about 1:6. In some embodiments, the acetonitrile to water ratio (volume:volume) is about 9:1, 8:1, 7:1, 6:1, 5:1, 4:1, 3:1, 2:1, 1:1, 1:2, 1:3, 1:4, 1:5, 1:6, 1:7, 1:8, or about 1:9. In some embodiments, the acetonitrile to water ratio (volume:volume) is about 1:3 or about 1:4.

Form III

In some embodiments, the present invention provides a method of preparing Form III of Compound I of the present invention, including forming a mixture of Compound I of the present invention, and a solvent, under conditions suitable to prepare Form III. Any suitable solvent can be used in the method of preparing Compound I Form III. In some embodiments, the method of preparing Form III of Compound I comprises heating Compound I in a solvent, then cooling the mixture to provide Form III. In some embodiments, the solvent can be at least one of water, methanol, ethanol, isopropanol, methyl ethyl ketone (i.e., 2-butanone), acetone, acetonitrile, isobutyl acetate, ethyl acetate, or methyl tert-butyl ether. In some embodiments, the solvent can be at least one of water, methanol, isopropanol, or acetonitrile. In some embodiments, the solvent can include one of water, methanol, isopropanol, or acetonitrile.

Therapeutic and Prophylactic Uses

The present invention contemplates the use of the solid forms of Compound I described herein in the treatment or prevention of a broad range of diseases, disorders and/or conditions, and/or the symptoms thereof. While particular uses are described in detail hereafter, it is to be understood that the present invention is not so limited. Furthermore, although general categories of particular diseases, disorders and conditions are set forth hereafter, some of the diseases, disorders and conditions may be a member of more than one category, and others may not be a member of any of the disclosed categories.

In some embodiments, the diseases, disorders and/or conditions described herein are mediated, at least in part, by the adenosine $A_{2A}$ receptor ($A_{2A}R$). In some embodiments, the diseases, disorders and/or conditions described herein are mediated, at least in part, by the adenosine $A_{2B}$ receptor ($A_{2B}R$). In some embodiments, the diseases, disorders and/or conditions described herein are mediated, at least in part, by both $A_{2A}R$ and $A_{2B}R$.

In some embodiments, the solid forms of Compound I described herein are administered in an amount effective to reverse or stop the progression of $A_{2A}R$-mediated immunosuppression.

Oncology-related Disorders. In accordance with the present invention, a solid form of Compound I can be used to treat or prevent a proliferative condition or disorder, including a cancer, for example, cancer of the uterus, cervix, breast, prostate, testes, gastrointestinal tract (e.g., esophagus, oropharynx, stomach, small or large intestines, colon, or rectum), kidney, renal cell, bladder, bone, bone marrow, skin, head or neck, liver, gall bladder, heart, lung, pancreas, salivary gland, adrenal gland, thyroid, brain (e.g., gliomas), ganglia, central nervous system (CNS) and peripheral nervous system (PNS), and cancers of the hematopoietic system and the immune system (e.g., spleen or thymus). The present invention also provides methods of treating or preventing other cancer-related diseases, disorders or conditions, including, for example, immunogenic tumors, non-immunogenic tumors, dormant tumors, virus-induced cancers (e.g., epithelial cell cancers, endothelial cell cancers, squamous cell carcinomas and papillomavirus), adenocarcinomas, lymphomas, carcinomas, melanomas, leukemias, myelomas, sarcomas, teratocarcinomas, chemically-induced cancers, metastasis, and angiogenesis. The invention contemplates reducing tolerance to a tumor cell or cancer cell antigen, e.g., by modulating activity of a regulatory T-cell and/or a CD8+ T-cell (see, e.g., Ramirez-Montagut, et al. (2003) *Oncogene* 22:3180-87; and Sawaya, et al. (2003) *New Engl. J. Med.* 349:1501-09). In particular embodiments, the tumor or cancer is colon cancer, ovarian cancer, breast cancer, melanoma, lung cancer, glioblastoma, or leukemia. The use of the term(s) cancer-related diseases, disorders and conditions is meant to refer broadly to conditions that are associated, directly or indirectly, with cancer, and includes, e.g., angiogenesis and precancerous conditions such as dysplasia.

In certain embodiments, a cancer may be metastatic or at risk of becoming metastatic, or may occur in a diffuse tissue, including cancers of the blood or bone marrow (e.g., leukemia). In some further embodiments, the compounds of the invention can be used to overcome T-cell tolerance.

In some embodiments, the present invention provides methods for treating a proliferative condition, cancer, tumor, or precancerous condition with a solid form of Compound I and at least one additional therapeutic or diagnostic agent, examples of which are set forth elsewhere herein.

Immune- and Inflammatory-related Disorders. As used herein, terms such as "immune disease", "immune condition", "immune disorder", "inflammatory disease", "inflammatory condition", "inflammatory disorder" and the like are meant to broadly encompass any immune-related condition (e.g., an autoimmune disease) or a disorder with an inflammatory component that can be treated by the solid forms of Compound I described herein such that some therapeutic benefit is obtained. Such conditions frequently are inextricably intertwined with other diseases, disorders and conditions. By way of example, an "immune condition" may refer to proliferative conditions, such as cancer, tumors, and angiogenesis; including infections (acute and chronic), tumors, and cancers that resist eradication by the immune system.

The solid forms of Compound I of the present invention can be used to increase or enhance an immune response; to improve immunization, including increasing vaccine efficacy; and to increase inflammation. Immune deficiencies associated with immune deficiency diseases, immunosuppressive medical treatment, acute and/or chronic infection, and aging can be treated using the compounds disclosed herein. The solid forms of Compound I can also be used to stimulate the immune system of patients suffering from iatrogenically-induced immune suppression, including those who have undergone bone marrow transplants, chemotherapy, or radiotherapy.

In particular embodiments of the present disclosure, the solid forms of Compound I are used to increase or enhance an immune response to an antigen by providing adjuvant activity. In a particular embodiment, at least one antigen or vaccine is administered to a subject in combination with at least one solid form of Compound I of the present invention to prolong an immune response to the antigen or vaccine. Therapeutic compositions are also provided which include at least one antigenic agent or vaccine component, including, but not limited to, viruses, bacteria, and fungi, or portions thereof, proteins, peptides, tumor-specific antigens, and nucleic acid vaccines, in combination with at least one solid form of Compound I of the present invention.

A non-limiting list of immune- and inflammatory-related diseases, disorders and conditions which may be treated or prevented with the compounds and compositions of the present invention include, arthritis (e.g., rheumatoid arthritis), kidney failure, lupus, asthma, psoriasis, colitis, pancreatitis, allergies, fibrosis, surgical complications (e.g., where inflammatory cytokines prevent healing), anemia, and fibromyalgia. Other diseases and disorders which may be associated with chronic inflammation include Alzheimer's disease, congestive heart failure, stroke, aortic valve stenosis, arteriosclerosis, osteoporosis, Parkinson's disease, infections, inflammatory bowel disease (e.g., Crohn's disease and ulcerative colitis), allergic contact dermatitis and other eczemas, systemic sclerosis, transplantation and multiple sclerosis.

Among other immune-related disorders, it is contemplated that inhibition of $A_{2A}R/A_{2B}R$ function may also play a role in immunologic tolerance and prevention of fetal rejection in utero.

In some embodiments, a solid form of the $A_{2A}R/A_{2B}R$ inhibitor Compound I described herein can be combined with an immunosuppressive agent to reduce the number of immune effector cells.

Some of the aforementioned diseases, disorders and conditions for which an $A_{2A}R/A_{2B}R$ inhibitor may be particularly efficacious (due to, for example, limitations of current therapies) are described in more detail hereafter.

Rheumatoid Arthritis (RA), which is generally characterized by chronic inflammation in the membrane lining (the synovium) of the joints, affects approximately 1% of the U.S. population (~2.1 million people). Further understanding of the role of cytokines, including TNF-α and IL-1, in the inflammatory process has enabled the development and introduction of a new class of disease-modifying antirheumatic drugs (DMARDs). Agents (some of which overlap with treatment modalities for RA) include ENBREL (etanercept), REMICADE (infliximab), HUMIRA (adalimumab) and KINERET (anakinra) Though some of these agents relieve symptoms, inhibit progression of structural damage, and improve physical function in particular patient populations, there is still a need for alternative agents with improved efficacy, complementary mechanisms of action, and fewer/less severe adverse effects.

Psoriasis, a constellation of common immune-mediated chronic skin diseases, affects more than 4.5 million people in the U.S., of which 1.5 million are considered to have a moderate-to severe form of the disease. Moreover, over 10% of patients with psoriasis develop psoriatic arthritis, which damages the bone and connective tissue around the joints. An improved understanding of the underlying physiology of psoriasis has resulted in the introduction of agents that, for example, target the activity of T lymphocytes and cytokines responsible for the inflammatory nature of the disease. Such agents include the TNF-α inhibitors (also used in the treatment of rheumatoid arthritis (RA)), including ENBREL (etanercept), REMICADE (infliximab) and HUMIRA (adalimumab)), and T-cell inhibitors such as AMEVIVE (alefacept) and RAPTIVA (efalizumab). Though several of these agents are effective to some extent in certain patient populations, none have been shown to effectively treat all patients.

Microbial-related Disorders. The present invention contemplates the use of the solid form of the $A_{2A}R/A_{2B}R$ inhibitor Compound I described herein in the treatment and/or prevention of any viral, bacterial, fungal, parasitic or other infective disease, disorder or condition for which treatment with an $A_{2A}R/A_{2B}R$ inhibitor may be beneficial.

Examples of viral diseases, disorders and conditions that are contemplated include, but are not limited to, hepatitis B virus (HBV), hepatitis C virus (HCV), human papilloma virus (HPV), HIV, AIDS (including its manifestations such as cachexia, dementia, and diarrhea), herpes simplex virus (HSV), Epstein-Barr virus (EBV), varicella zoster virus, coxsackie virus, and cytomegalovirus (CMV).

Further examples of such diseases and disorders include staphylococcal and streptococcal infections (e.g., *Staphylococcus aureus* and *streptococcus sanguinis*, respectively), *leishmania, toxoplasma, trichomonas, giardia, Candida albicans, Bacillus anthracis*, and *Pseudomonas aeruginosa*. In some embodiments, diseases or disorders include *Mycobacterium* infection (e.g., *Mycobacterium leprae* or *Mycobacterium tuberculosis*) or an infection caused by *Listeria monocytogenes* or *Toxoplasma gondii*. Solid forms of Compound I of the invention can be used to treat sepsis, decrease or inhibit bacterial growth, and reduce or inhibit inflammatory cytokines.

Further embodiments contemplate the treatment of a parasitic infection including, but not limited to, *Leishmania donovani, Leishmania tropica, Leishmania major, Leishmania aethiopica, Leishmania mexicana, Plasmodium falciparum, Plasmodium vivax, Plasmodium ovale*, or *Plasmodium malariae*. Frequently, anti-parasitic therapy is administered prophylactically (e.g., before a subject travels to an area with a high frequency of parasitic infection).

CNS-related and Neurological Disorders. Inhibition of $A_{2A}R/A_{2B}R$ by a solid form of Compound I may also be an important treatment strategy for patients with neurological, neuropsychiatric, neurodegenerative or other diseases, disorders and conditions having some association with the central nervous system, including disorders associated with impairment of cognitive function and motor function. Examples include Parkinson's disease, extra pyramidal syndrome (EPS), dystonia, akathisia, tardive dyskinesia, restless leg syndrome (RLS), epilepsy, periodic limb movement in sleep (PLMS), attention deficit disorders, depression, anxiety, dementia, Alzheimer's disease, Huntington's disease, multiple sclerosis, cerebral ischemia, hemorrhagic stroke, subarachnoid hemorrhage, and traumatic brain injury.

Subjects suffering from multiple sclerosis (MS), a seriously debilitating autoimmune disease comprising multiple areas of inflammation and scarring of the myelin in the brain and spinal cord, may be particularly helped by the solid forms of Compound I described herein, as current treatments only alleviate symptoms or delay the progression of disability.

Similarly, the solid forms of Compound I may be particularly advantageous for subjects afflicted with neurodegenerative disorders, such as Alzheimer's disease (AD), a brain disorder that seriously impairs patients' thought, memory, and language processes; and Parkinson's disease (PD), a progressive disorder of the CNS characterized by, for example, abnormal movement, rigidity and tremor. These disorders are progressive and debilitating, and no curative agents are available.

Other Disorders. Embodiments of the present invention contemplate the administration of the solid forms of Compound I described herein to a subject for the treatment or prevention of any other disorder that may benefit from at least some level of $A_{2A}R/A_{2B}R$ inhibition. Such diseases, disorders and conditions include, for example, cardiovascular (e.g., cardiac ischemia), gastrointestinal (e.g., Crohn's disease), metabolic (e.g., diabetes), hepatic (e.g., hepatic fibrosis, NASH, and NAFLD), pulmonary (e.g., COPD and asthma), ophthalmologic (e.g., diabetic retinopathy), and renal (e.g., renal failure) disorders.

Pharmaceutical Compositions

The solid forms of Compound I of the present invention may be in the form of compositions suitable for administration to a subject. In general, such compositions are "pharmaceutical compositions" comprising the solid form(s) of Compound I and one or more pharmaceutically acceptable or physiologically acceptable diluents, carriers or excipients. In certain embodiments, the solid forms of Compound I are present in a therapeutically acceptable amount. The pharmaceutical compositions may be used in the methods of the present invention; thus, for example, the pharmaceutical compositions can be administered ex vivo or in vivo to a subject in order to practice the therapeutic and prophylactic methods and uses described herein.

The pharmaceutical compositions of the present invention can be formulated to be compatible with the intended method or route of administration; exemplary routes of administration are set forth herein. Furthermore, the pharmaceutical compositions may be used in combination with other therapeutically active agents or compounds as described herein in order to treat or prevent the diseases, disorders and conditions as contemplated by the present invention.

The pharmaceutical compositions containing the active ingredient (e.g., a solid form of the inhibitor Compound I of $A_{2A}R/A_{2B}R$ function) may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylene-vinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly (methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinylpyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxy-ethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified herein.

The pharmaceutical compositions of the present invention may also be in the form of oil-in-water emulsions. The oily phase may be a vegetable oil, for example olive oil or *arachis* oil, or a mineral oil, for example, liquid paraffin, or mixtures of these. Suitable emulsifying agents may be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

The pharmaceutical compositions typically comprise a therapeutically effective amount of the solid form of Compound I contemplated by the present invention and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), and N-tris[Hydroxymethyl]methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampoule, syringe, or autoinjector (similar to, e.g., an EpiPen®)), whereas a multi-use container (e.g., a multi-use vial) is provided in other embodiments.

Formulations can also include carriers to protect the composition against rapid degradation or elimination from the body, such as a controlled release formulation, including liposomes, hydrogels, prodrugs and microencapsulated delivery systems. For example, a time delay material such as glyceryl monostearate or glyceryl stearate alone, or in combination with a wax, may be employed. Any drug delivery apparatus may be used to deliver a solid form of the $A_{2A}R/A_{2B}R$ inhibitor Compound I, including implants (e.g., implantable pumps) and catheter systems, slow injection pumps and devices, all of which are well known to the skilled artisan.

Depot injections, which are generally administered subcutaneously or intramuscularly, may also be utilized to release the $A_{2A}R/A_{2B}R$ inhibitors disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions may be in the form of a sterile injectable aqueous or oleagenous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor EL™ (BASF, Parsippany, NJ) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose any bland fixed oil may be employed, including synthetic mono- or diglycerides. Moreover, fatty acids such as oleic acid, find use in the preparation of injectables. Prolonged absorption of particular injectable formulations can be achieved by including an agent that delays absorption (e.g., aluminum monostearate or gelatin).

The present invention contemplates the administration of the solid forms of Compound I in the form of suppositories for rectal administration. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

The solid forms of Compound I contemplated by the present invention may be in the form of any other suitable pharmaceutical composition (e.g., sprays for nasal or inhalation use) currently known or developed in the future.

Routes of Administration

The present invention contemplates the administration of the solid forms of Compound I, and compositions thereof, in any appropriate manner. Suitable routes of administration include oral, parenteral (e.g., intramuscular, intravenous, subcutaneous (e.g., injection or implant), intraperitoneal, intracisternal, intraarticular, intracerebral (intraparenchymal) and intracerebroventricular), nasal, vaginal, sublingual, intraocular, rectal, topical (e.g., transdermal), buccal and inhalation. Depot injections, which are generally administered subcutaneously or intramuscularly, may also be utilized to release the solid forms of Compound I disclosed herein over a defined period of time.

Particular embodiments of the present invention contemplate oral administration.

Combination Therapy

The present invention contemplates the use of the solid forms of Compound I in combination with one or more active therapeutic agents (e.g., chemotherapeutic agents) or other prophylactic or therapeutic modalities (e.g., radiation). In such combination therapy, the various active agents frequently have different, complementary mechanisms of action. Such combination therapy may be especially advantageous by allowing a dose reduction of one or more of the agents, thereby reducing or eliminating the adverse effects associated with one or more of the agents. Furthermore, such combination therapy may have a synergistic therapeutic or prophylactic effect on the underlying disease, disorder, or condition.

As used herein, "combination" is meant to include therapies that can be administered separately, for example, formulated separately for separate administration (e.g., as may be provided in a kit), and therapies that can be administered together in a single formulation (i.e., a "co-formulation").

In certain embodiments, the solid forms of Compound I are administered or applied sequentially, e.g., where one agent is administered prior to one or more other agents. In other embodiments, the solid forms of Compound I are administered simultaneously, e.g., where two or more agents are administered at or about the same time; the two or more agents may be present in two or more separate formulations or combined into a single formulation (i.e., a co-formulation). Regardless of whether the two or more agents are administered sequentially or simultaneously, they are considered to be administered in combination for purposes of the present invention.

The solid forms of Compound I of the present invention may be used in combination with at least one other (active) agent in any manner appropriate under the circumstances. In one embodiment, treatment with the at least one active agent and at least one solid form of Compound I of the present invention is maintained over a period of time. In another embodiment, treatment with the at least one active agent is reduced or discontinued (e.g., when the subject is stable), while treatment with a solid form of Compound I of the present invention is maintained at a constant dosing regimen. In a further embodiment, treatment with the at least one active agent is reduced or discontinued (e.g., when the subject is stable), while treatment with the solid form of Compound I of the present invention is reduced (e.g., lower dose, less frequent dosing or shorter treatment regimen). In yet another embodiment, treatment with the at least one active agent is reduced or discontinued (e.g., when the subject is stable), and treatment with the solid form of Compound I of the present invention is increased (e.g., higher dose, more frequent dosing or longer treatment regimen). In yet another embodiment, treatment with the at least one active agent is maintained and treatment with the solid form of Compound I of the present invention is reduced or discontinued (e.g., lower dose, less frequent dosing or shorter treatment regimen). In yet another embodiment, treatment with the at least one active agent and treatment with the solid form of the present invention are reduced or discontinued (e.g., lower dose, less frequent dosing or shorter treatment regimen).

Oncology-related Disorders. The present invention provides methods for treating and/or preventing a proliferative condition, cancer, tumor, or precancerous disease, disorder or condition with a solid form of Compound I and at least one additional therapeutic or diagnostic agent. In some embodiments, the additional therapeutic or diagnostic agent is radiation, an immunomodulatory agent or chemotherapeutic agent, or diagnostic agent. Suitable immunomodulatory agents that may be used in the present invention include CD40L, B7, and B7RP1; activating monoclonal antibodies (mAbs) to stimulatory receptors, such as, ant-CD40, anti-CD38, anti-ICOS, and 4-IBB ligand; dendritic cell antigen loading (in vitro or in vivo); anti-cancer vaccines such as dendritic cell cancer vaccines; cytokines/chemokines, such as, IL1, IL2, IL12, IL18, ELC/CCL19, SLC/CCL21, MCP-1, IL-4, IL-18, TNF, IL-15, MDC, IFNa/b, M-CSF, IL-3, GM-CSF, IL-13, and anti-IL-10; bacterial lipopolysaccharides (LPS); and immune-stimulatory oligonucleotides.

In certain embodiments, the present invention provides methods for tumor suppression of tumor growth comprising administration of a solid form of Compound I described herein in combination with a signal transduction inhibitor (STI) to achieve additive or synergistic suppression of tumor growth. As used herein, the term "signal transduction inhibitor" refers to an agent that selectively inhibits one or more steps in a signaling pathway. Signal transduction inhibitors (STIs) of the present invention include: (i) bcr/abl kinase inhibitors (e.g., GLEEVEC); (ii) epidermal growth factor (EGF) receptor inhibitors, including kinase inhibitors and antibodies; (iii) her-2/neu receptor inhibitors (e.g., HERCEPTIN); (iv) inhibitors of Akt family kinases or the Akt pathway (e.g., rapamycin); (v) cell cycle kinase inhibitors (e.g., flavopiridol); and (vi) phosphatidyl inositol kinase inhibitors. Agents involved in in immunomodulation can also be used in combination with the $A_{2A}R/A_{2B}R$ inhibitors described herein for the suppression of tumor growth in cancer patients.

Examples of chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide, and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel and docetaxel; chlorambucil; gemcitabine; 6-thioguanine; mercaptopurine; methotrexate; platinum and platinum coordination complexes such as cisplatin, carboplatin, and oxaliplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitors; difluoromethylornithine (DMFO); retinoic acid; esperamicins; capecitabine; anthracyclines; and pharmaceutically acceptable salts, acids or derivatives of any of the above.

Chemotherapeutic agents also include anti-hormonal agents that act to regulate or inhibit hormonal action on tumors such as anti-estrogens, including for example tamoxifen, raloxifene, aromatase inhibiting 4(5)-imidazoles, 4-hydroxytamoxifen, trioxifene, keoxifene, onapristone, and toremifene; and antiandrogens such as flutamide, nilutamide, bicalutamide, leuprolide, and goserelin; and pharmaceutically acceptable salts, acids or derivatives of any of the above. In certain embodiments, combination therapy comprises a chemotherapy regimen that includes one or more chemotherapeutic agents. In certain embodiments, combination therapy comprises administration of a hormone or related hormonal agent.

Additional treatment modalities that may be used in combination with a solid form of Compound I include radiotherapy, a monoclonal antibody against a tumor antigen, a complex of a monoclonal antibody and toxin, a T-cell adjuvant, bone marrow transplant, or antigen presenting cells (e.g., dendritic cell therapy).

Immune Checkpoint Inhibitors. The present invention contemplates the use of the solid forms of the inhibitor Compound I of $A_{2A}R/A_{2B}R$ function described herein in combination with immune checkpoint inhibitors.

The tremendous number of genetic and epigenetic alterations that are characteristic of all cancers provides a diverse set of antigens that the immune system can use to distinguish tumor cells from their normal counterparts. In the case of T cells, the ultimate amplitude (e.g., levels of cytokine production or proliferation) and quality (e.g., the type of immune response generated, such as the pattern of cytokine production) of the response, which is initiated through antigen recognition by the T-cell receptor (TCR), is regulated by a balance between co-stimulatory and inhibitory signals (immune checkpoints). Under normal physiological conditions, immune checkpoints are crucial for the prevention of autoimmunity (i.e., the maintenance of self-tolerance) and also for the protection of tissues from damage when the immune system is responding to pathogenic infection. The expression of immune checkpoint proteins can be dysregulated by tumors as an important immune resistance mechanism.

T-cells have been the major focus of efforts to therapeutically manipulate endogenous antitumor immunity because of i) their capacity for the selective recognition of peptides derived from proteins in all cellular compartments; ii) their capacity to directly recognize and kill antigen-expressing cells (by CD8+ effector T cells; also known as cytotoxic T lymphocytes (CTLs)); and iii) their ability to orchestrate diverse immune responses by CD4+ helper T cells, which integrate adaptive and innate effector mechanisms.

In the clinical setting, the blockade of immune checkpoints which results in the amplification of antigen-specific T cell responses has shown to be a promising approach in human cancer therapeutics.

T cell-mediated immunity includes multiple sequential steps, each of which is regulated by counterbalancing stimulatory and inhibitory signals in order to optimize the response. While nearly all inhibitory signals in the immune response ultimately modulate intracellular signaling pathways, many are initiated through membrane receptors, the ligands of which are either membrane-bound or soluble (cytokines). While co-stimulatory and inhibitory receptors and ligands that regulate T-cell activation are frequently not over-expressed in cancers relative to normal tissues, inhibitory ligands and receptors that regulate T cell effector functions in tissues are commonly overexpressed on tumor cells or on non-transformed cells associated with the tumor microenvironment. The functions of the soluble and membrane-bound receptor ligand immune checkpoints can be modulated using agonist antibodies (for co-stimulatory pathways) or antagonist antibodies (for inhibitory pathways). Thus, in contrast to most antibodies currently approved for cancer therapy, antibodies that block immune checkpoints do not target tumor cells directly, but rather target lymphocyte receptors or their ligands in order to enhance endogenous antitumor activity. [See Pardoll, (April 2012) Nature Rev. Cancer 12:252-64].

Examples of immune checkpoints (ligands and receptors), some of which are selectively upregulated in various types of tumor cells, that are candidates for blockade include PD1 (programmed cell death protein 1); PDL1 (PD1 ligand); BTLA (B and T lymphocyte attenuator); CTLA4 (cytotoxic T-lymphocyte associated antigen 4); TIM3 (T-cell membrane protein 3); LAG3 (lymphocyte activation gene 3); TIGIT (T cell immunoreceptor with Ig and ITIM domains); and Killer Inhibitory Receptors, which can be divided into two classes based on their structural features: i) killer cell immunoglobulin-like receptors (KIRs), and ii) C-type lectin receptors (members of the type II transmembrane receptor family). Other less well-defined immune checkpoints have been described in the literature, including both receptors (e.g., the 2B4 (also known as CD244) receptor) and ligands (e.g., certain B7 family inhibitory ligands such B7-H3 (also known as CD276) and B7-H4 (also known as B7-S1, B7x and VCTN1)). [See Pardoll, (April 2012) Nature Rev. Cancer 12:252-64].

The present invention contemplates the use of the solid forms of inhibitor Compound I of $A_{2A}R/A_{2B}R$ function described herein in combination with inhibitors of the aforementioned immune-checkpoint receptors and ligands, as well as yet-to-be-described immune-checkpoint receptors and ligands. Certain modulators of immune checkpoints are currently available, whereas others are in late-stage development. To illustrate, when it was approved for the treatment of melanoma in 2011, the fully humanized CTLA4 monoclonal antibody ipilimumab (YERVOY; Bristol-Myers Squibb) became the first immune checkpoint inhibitor to receive regulatory approval in the US. Fusion proteins comprising CTLA4 and an antibody (CTLA4-Ig; abatcept (ORENCIA; Bristol-Myers Squibb)) have been used for the treatment of rheumatoid arthritis, and other fusion proteins have been shown to be effective in renal transplantation patients that are sensitized to Epstein Barr Virus. PD1 antibodies are under development (e.g., nivolumab (Bristol-Myers Squibb) and lambrolizumab (Merck)), and anti-PDL1 antibodies are also being evaluated (e.g., MPDL3280A (Roche)). Nivolumab has shown promise in patients with melanoma, lung and kidney cancer.

In one aspect of the present invention, the claimed solid forms of Compound I are combined with an immuno-oncology agent that is (i) an agonist of a stimulatory (including a co-stimulatory) receptor or (ii) an antagonist of an inhibitory (including a co-inhibitory) signal on T cells, both of which result in amplifying antigen-specific T cell responses. Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LT13R, LIGHT, DcR3, HVEM, VEGI/TL1A, TRAMP/DR3, EDAR, EDA1, XEDAR, EDA2, TNFR1, Lymphotoxin a/TNF13, TNFR2, TNFa, LT13R, Lymphotoxin a 1132, FAS, FASL, RELT, DR6, TROY, NGFR.

In another aspect, the immuno-oncology agent is a cytokine that inhibits T cell activation (e.g., IL-6, IL-10, TGF-B, VEGF, and other immunosuppressive cytokines) or a cytokine that stimulates T cell activation, for stimulating an immune response.

In one aspect, T cell responses can be stimulated by a combination of the disclosed $A_{2A}R/A_{2B}R$ inhibitors and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and/or (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD2. Other agents that can be combined with the $A_{2A}R/A_{2B}R$ inhibitors of the present invention for the treatment of cancer include antagonists of inhibitory receptors on NK cells or agonists of activating receptors on NK cells. For example, compounds herein can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In another aspect, the disclosed $A_{2A}R/A_{2B}R$ inhibitors can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY (ipilimumab) or tremelimumab.

In another aspect, the immuno-oncology agent is a PD-1 antagonist, such as an antagonistic PD-1 antibody. Suitable PD-1 antibodies include, for example, OPDIVO (nivolumab), KEYTRUDA (pembrolizumab), or MEDI-0680 (AMP-514; WO2012/145493). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224.

In another aspect, the immuno-oncology agent is a PD-L1 antagonist, such as an antagonistic PD-L1 antibody. Suitable PD-L1 antibodies include, for example, MPDL3280A (RG7446; WO2010/077634), durvalumab (MEDI4736), BMS-936559 (WO2007/005874), and MSB0010718C (WO2013/79174).

In another aspect, the immuno-oncology agent is a LAG-3 antagonist, such as an antagonistic LAG-3 antibody. Suitable LAG3 antibodies include, for example, BMS-986016 (WO10/19570, WO14/08218), or IMP-731 or IMP-321 (WO08/132601, WO09/44273).

In another aspect, the immuno-oncology agent is a CD137 (4-1BB) agonist, such as an agonistic CD137 antibody. Suitable CD137 antibodies include, for example, urelumab and PF-05082566 (WO12/32433).

In another aspect, the immuno-oncology agent is a GITR agonist, such as an agonistic GITR antibody. Suitable GITR antibodies include, for example, BMS-986153, BMS-986156, TRX-518 (WO06/105021, WO09/009116) and MK-4166 (WO11/028683).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO11/109400).

The present invention encompasses pharmaceutically acceptable salts, acids or derivatives of any of the above.

Metabolic and Cardiovascular Diseases. The present invention provides methods for treating and/or preventing certain cardiovascular- and/or metabolic-related diseases, disorders and conditions, as well as disorders associated therewith, with a solid form of the $A_{2A}R/A_{2B}R$ inhibitor Compound I and at least one additional therapeutic or diagnostic agent.

Examples of therapeutic agents useful in combination therapy for the treatment of hypercholesterolemia (and atherosclerosis as well) include statins (e.g., CRESTOR, LESCOL, LIPITOR, MEVACOR, PRAVACOL, and ZOCOR), which inhibit the enzymatic synthesis of cholesterol; bile acid resins (e.g., COLESTID, LO-CHOLEST, PREVALITE, QUESTRAN, and WELCHOL), which sequester cholesterol and prevent its absorption; ezetimibe (ZETIA), which blocks cholesterol absorption; fibric acid (e.g., TRICOR), which reduces triglycerides and may modestly increase HDL; niacin (e.g., NIACOR), which modestly lowers LDL cholesterol and triglycerides; and/or a combination of the aforementioned (e.g., VYTORIN (ezetimibe with simvastatin). Alternative cholesterol treatments that may be candidates for use in combination with the $A_{2A}R/A_{2B}R$ inhibitors described herein include various supplements and herbs (e.g., garlic, policosanol, and guggul).

The present invention encompasses pharmaceutically acceptable salts, acids or derivatives of any of the above.

Immune- and Inflammatory-related Disorders. The present invention provides methods for treating and/or preventing immune-related diseases, disorders and conditions; and diseases, disorders and conditions having an inflammatory component; with a solid form of the $A_{2A}R/A_{2B}R$ inhibitor Compound I and at least one additional therapeutic or diagnostic agent.

Examples of therapeutic agents useful in combination therapy include, but are not limited to, the following: non-steroidal anti-inflammatory drug (NSAID) such as aspirin, ibuprofen, and other propionic acid derivatives (alminoprofen, benoxaprofen, bucloxic acid, carprofen, fenbufen, fenoprofen, fluprofen, flurbiprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, fuirofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone). Other combinations include cyclooxygenase-2 (COX-2) inhibitors.

Other active agents for combination include steroids such as prednisolone, prednisone, methylprednisolone, betamethasone, dexamethasone, or hydrocortisone. Such a combination may be especially advantageous since one or more adverse effects of the steroid can be reduced or even eliminated by tapering the steroid dose required.

Additional examples of active agents that may be used in combinations for treating, for example, rheumatoid arthritis, include cytokine suppressive anti-inflammatory drug(s) (CSAIDs); antibodies to, or antagonists of, other human cytokines or growth factors, for example, TNF, LT, IL-10, IL-2, IL-6, IL-7, IL-8, IL-15, IL-16, IL-18, EMAP-II, GM-CSF, FGF, or PDGF.

Particular combinations of active agents may interfere at different points in the autoimmune and subsequent inflammatory cascade, and include TNF antagonists such as chimeric, humanized or human TNF antibodies, REMICADE, anti-TNF antibody fragments (e.g., CDP870), and soluble p55 or p75 TNF receptors, derivatives thereof, p75TNFR1gG (ENBREL.) or p55TNFR1gG (LENERCEPT), soluble IL-13 receptor (sIL-13), and also TNFa-converting enzyme (TACE) inhibitors; similarly, IL-1 inhibitors (e.g., Interleukin-1-converting enzyme inhibitors) may be effective. Other combinations include Interleukin 11, anti-P7s and p-selectin glycoprotein ligand (PSGL). Other examples of agents useful in combination with the $A_{2A}R/A_{2B}R$ inhibitors described herein include interferon-131a (AVONEX); interferon-131b (BETASERON); copaxone; hyperbaric oxygen; intravenous immunoglobulin; clabribine; and antibodies to, or antagonists of, other human cytokines or growth factors (e.g., antibodies to CD40 ligand and CD80).

Microbial Diseases. The present invention provides methods for treating and/or preventing viral, bacterial, fungal and parasitic diseases, disorders and conditions, as well as disorders associated therewith, with a solid form of the $A_{2A}R/A_{2B}R$ inhibitor Compound I and at least one additional therapeutic or diagnostic agent (e.g., one or more other antiviral agents and/or one or more agents not associated with viral therapy).

Such combination therapy includes anti-viral agents targeting various viral life-cycle stages and having different mechanisms of action, including, but not limiting to, the following: inhibitors of viral uncoating (e.g., amantadine and rimantidine); reverse transcriptase inhibitors (e.g., acyclovir, zidovudine, and lamivudine); agents that target integrase; agents that block attachment of transcription factors to viral DNA; agents (e.g., antisense molecules) that impact translation (e.g., fomivirsen); agents that modulate translation/ribozyme function; protease inhibitors; viral assembly modulators (e.g., rifampicin); antiretrovirals such as, for example, nucleoside analogue reverse transcriptase inhibitors (e.g., azidothymidine (AZT), ddl, ddC, 3TC, d4T); non-nucleoside reverse transcriptase inhibitors (e.g., efavirenz, nevirapine); nucleotide analogue reverse transcriptase inhibitors; and agents that prevent release of viral particles (e.g., zanamivir and oseltamivir). Treatment and/or prevention of certain viral infections (e.g., HIV) frequently entail a group ("cocktail") of antiviral agents.

Other antiviral agents contemplated for use in combination with a solid form of Compound I include, but are not limited to, the following: abacavir, adefovir, amantadine, amprenavir, ampligen, arbidol, atazanavir, atripla, boceprevirertet, cidofovir, combivir, darunavir, delavirdine, didanosine, docosanol, edoxudine, emtricitabine, enfuvirtide, entecavir, famciclovir, fosamprenavir, foscarnet, fosfonet, http://en.wikipedia.org/wiki/Fusion_inhibitor ganciclovir, ibacitabine, imunovir, idoxuridine, imiquimod, indinavir, inosine, various interferons (e.g., peginterferon alfa-2a), lopinavir, loviride, maraviroc, moroxydine, methisazone, nelfinavir, nexavir, penciclovir, peramivir, pleconaril, podophyllotoxin, raltegravir, ribavirin, ritonavir, pyramidine, saquinavir, stavudine, telaprevir, tenofovir, tipranavir, trifluridine, trizivir, tromantadine, truvada, valaciclovir, valganciclovir, vicriviroc, vidarabine, viramidine, and zalcitabine.

The present invention contemplates the use of the solid forms of Compound I function described herein in combination with antiparasitic agents. Such agents include, but are not limited to, thiabendazole, pyrantel pamoate, mebendazole, praziquantel, niclosamide, bithionol, oxamniquine, metrifonate, ivermectin, albendazole, eflornithine, melarsoprol, pentamidine, benznidazole, nifurtimox, and nitroimidazole. The skilled artisan is aware of other agents that may find utility for the treatment of parasitic disorders.

Embodiments of the present invention contemplate the use of the solid forms of Compound I described herein in combination with agents useful in the treatment or prevention of bacterial disorders. Antibacterial agents can be classified in various manners, including based on mechanism of action, based on chemical structure, and based on spectrum of activity. Examples of antibacterial agents include those that target the bacterial cell wall (e.g., cephalosporins and penicillins) or the cell membrane (e.g., polymyxins), or interfere with essential bacterial enzymes (e.g., sulfonamides, rifamycins, and quinolines). Most antibacterial agents that target protein synthesis (e.g., tetracyclines and macrolides) are bacteriostatic, whereas agents such as the aminoglycoside are bactericidal. Another means of categorizing antibacterial agents is based on their target specificity; "narrow-spectrum" agents target specific types of bacteria (e.g., Gram-positive bacteria such as *Streptococcus*), while "broad-spectrum" agents have activity against a broader range of bacteria. The skilled artisan is aware of types of anti-bacterial agents that are appropriate for use in specific bacterial infections.

Embodiments of the present invention contemplate the use of the $A_{2A}R/A_{2B}R$ inhibitors described herein in combination with agents useful in the treatment or prevention of fungal disorders. Antifungal agents include polyenes (e.g., amphotericin, nystatin, and pimaricin); azoles (e.g., fluconazole, itraconazole, and ketoconazole); allylamines (e.g., naftifine, and terbinafine) and morpholines (e.g., amorolfine); and antimetabolies (e.g., 5-fluorocytosine).

The present invention encompasses pharmaceutically acceptable salts, acids or derivatives of the agents (and members of the classes of agents) set forth above.

Dosing

The solid forms of the $A_{2A}R/A_{2B}R$ inhibitor Compound I of the present invention may be administered to a subject in an amount that is dependent upon, for example, the goal of administration (e.g., the degree of resolution desired); the age, weight, sex, and health and physical condition of the subject to which the formulation is being administered; the route of administration; and the nature of the disease, disorder, condition or symptom thereof. The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (the maximum tolerated dose (MTD)) and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or ED50 of an agent is the dose or amount of an agent that produces a therapeutic response or desired effect in 50% of the population to which it is administered. Although the ED50 is commonly used as a measure of reasonable expectance of an agent's effect, it is not necessarily the dose that a clinician might deem appropriate taking into consideration all relevant factors. Thus, in some situations the effective amount is more than the calculated ED50, in other situations the effective amount is less than the calculated ED50, and in still other situations the effective amount is the same as the calculated ED50.

In addition, an effective dose of the solid forms of Compound I of the present invention may be an amount that, when administered in one or more doses to a subject, produces a desired result relative to a healthy subject. For example, for a subject experiencing a particular disorder, an effective dose may be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, or more than 90%, where 100% is defined as the diagnostic parameter, measure, marker and the like exhibited by a normal subject.

In certain embodiments, the solid forms of Compound I contemplated by the present invention may be administered (e.g., orally) at dosage levels of about 0.01 mg/kg to about 50 mg/kg, or about 1 mg/kg to about 25 mg/kg, of subject body weight per day, one or more times a day, to obtain the desired therapeutic effect.

For administration of an oral agent, the compositions can be provided in the form of tablets, capsules and the like containing from 1.0 to 1000.0 milligrams of the active ingredient, particularly 1.0, 3.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient.

In certain embodiments, the dosage of the desired the solid form of Compound I is contained in a "unit dosage form". The phrase "unit dosage form" refers to physically discrete units, each unit containing a predetermined amount of the solid form, either alone or in combination with one or more additional agents, sufficient to produce the desired effect. It will be appreciated that the parameters of a unit dosage form will depend on the particular agent and the effect to be achieved.

Kits

The present invention also contemplates kits comprising a the solid form of Compound I described herein, and pharmaceutical compositions thereof. The kits are generally in the form of a physical structure housing various components, as described below, and may be utilized, for example, in practicing the methods described above.

A kit can include one or more of the solid forms of Compound I disclosed herein (provided in, e.g., a sterile container), which may be in the form of a pharmaceutical composition suitable for administration to a subject. The solid forms of Compound I described herein can be provided in a form that is ready for use (e.g., a tablet or capsule) or in a form requiring, for example, reconstitution or dilution (e.g., a powder) prior to administration. When the solid forms of Compound I described herein are in a form that needs to be reconstituted or diluted by a user, the kit may also include diluents (e.g., sterile water), buffers, pharmaceutically acceptable excipients, and the like, packaged with or separately from the solid forms described herein. When combination therapy is contemplated, the kit may contain the several agents separately or they may already be combined in the kit. Each component of the kit may be enclosed within an individual container, and all of the various containers may be within a single package. A kit of the present invention may be designed for conditions necessary to properly maintain the components housed therein (e.g., refrigeration or freezing).

A kit may contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert may be, e.g., integrated into the physical structure housing the components, contained separately within the physical structure, or affixed to a component of the kit (e.g., an ampule, tube or vial).

Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via the internet, are provided.

EXPERIMENTAL

The following examples are put forth so as to provide those of ordinary skill in the art with a complete disclosure and description of how to make and use the present invention, and are not intended to limit the scope of what the inventors regard as their invention, nor are they intended to represent that the experiments below were performed or that they are all of the experiments that may be performed. It is to be understood that exemplary descriptions written in the present tense were not necessarily performed, but rather that the descriptions can be performed to generate data and the like of a nature described therein. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: wt=wildtype; bp=base pair(s); kb=kilobase(s); nt=nucleotides(s); aa=amino acid(s); s or sec=second(s); min=minute(s); h or hr=hour(s); ng=nanogram; g=microgram; mg=milligram; g=gram; kg=kilogram; dl or dL=deciliter; μl or L=microliter; ml or mL=milliliter; l or L=liter; M=micromolar; mM=millimolar; M=molar; kDa=kilodalton; i.m.=intramuscular(ly); i.p.=intraperitoneal(ly); SC or SQ=subcutaneous(ly); QD=daily; BID=twice daily; QW=weekly; QM=monthly; HPLC=high performance liquid chromatography; BW=body weight; U=unit; ns=not statistically significant; PBS=phosphate-buffered saline; IHC=immunohistochemistry; DMEM=Dulbeco's Modification of Eagle's Medium; EDTA=ethylenediaminetetraacetic acid.

Materials and Methods

The following general materials and methods were used, where indicated, or may be used in the Examples below:

The literature is replete with assays and other experimental techniques that can serve as a basis for evaluation of the compounds described herein.

X-Ray Powder Diffraction (XRPD)

XRPD analysis was carried out on a PANalytical X'pert pro, scanning the samples between 3 and 35° 2θ. The material was gently ground to release any agglomerates and loaded onto a multi-well plate with Kapton or Mylar polymer film to support the sample. The multi-well plate was then placed into the diffractometer and analyzed using Cu K radiation ($\alpha 1\lambda$=1.54060 Å; $\alpha 2$=1.54443 Å; $\beta$=1.39225 Å; $\alpha 1$: $\alpha 2$ ratio=0.5) running in transmission mode (step size 0.0130° 2θ) using 40 kV/40 mA generator settings.

Polarized Light Microscopy (PLM)

The presence of crystallinity (birefringence) was determined using an Olympus BX50 polarizing microscope, equipped with a Motic camera and image capture software (Motic Images Plus 2.0). All images were recorded using the 20× objective.

Differential Scanning Calorimetry (DSC)

Approximately 5 mg of material was weighed into an aluminium DSC pan and sealed non-hermetically with a pierced aluminium lid. The sample pan was then loaded into a Seiko DSC6200 (equipped with a cooler) cooled and held at 20° C. Once a stable heat-flow response was obtained, the sample and reference were heated to 230° C. at scan rate of 10° C./min and the resulting heat flow response monitored. Nitrogen was used as the purge gas, at a flow rate of 50 $cm^3$/min.

Thermogravimetric Analysis (TGA)

Approximately 5 mg of material was weighed into an open aluminium pan and loaded into a simultaneous thermogravimetric/differential thermal analyser (TG/DTA) and held at room temperature. The sample was then heated at a rate of 10° C./min from 20° C. to 300° C. during which time the change in sample weight was recorded along with any differential thermal events (DTA). Nitrogen was used as the purge gas, at a flow rate of 300 $cm^3$/min.

Dynamic Vapor Sorption (DVS)

Approximately 10 mg of sample was placed into a mesh vapor sorption balance pan and loaded into a DVS-1, DVS Intrinsic or DVS Advantage dynamic vapor sorption balance by Surface Measurement Systems. The sample was subjected to a ramping profile from 40-90% relative humidity (RH) at 10% increments, maintaining the sample at each step until a stable weight had been achieved (dm/dt 0.004%, minimum step length 30 min, maximum step length 500 min) at 25° C. After completion of the sorption cycle, the sample was dried using the same procedure to 0% RH and then a second sorption cycle back to 40% RH. Two cycles were performed. The weight change during the sorption/desorption cycles were plotted, allowing for the hygroscopic nature of the sample to be determined. XRPD analysis was then carried out on any solid retained.

Gravimetric Vapor Sorption (GVS)

Approximately 10-20 mg of sample was placed into a mesh vapor sorption balance pan and loaded into an IGASorp Moisture Sorption Analyser balance by Hiden Analytical. The sample was subjected to a ramping profile from 40-90% relative humidity (RH) at 10% increments, maintaining the sample at each step until a stable weight had been achieved (98% step completion, minimum step length 30 min, maximum step length 60 min) at 25° C. After completion of the sorption cycle, the sample was dried using the same procedure to 0% RH, and finally taken back to the starting point of 40% RH. Two cycles were performed. The weight change during the sorption/desorption cycles were plotted, allowing for the hygroscopic nature of the sample to be determined.

High Performance Liquid Chromatography-Ultraviolet Detection (HPLC-UV)

Instrument: Agilient 1100
Column: Zorbax Eclipse Plus C18 150 mm×3.0 mm, 3.5 μm particle size
Column Temperature: 35° C.
Autosampler Temperature: Ambient
UV wavelength: 228 nm
Injection Volume: 3 μL
Flow Rate: 1 mL/min
Mobile Phase A: Water (0.1% formic acid in 95:5 water:ACN)
Mobile Phase B: ACN (0.1% formic acid)
Gradient program:

| Time (minutes) | Solvent B [%] |
| --- | --- |
| 0 | 10 |
| 6 | 10 |
| 29 | 100 |
| 30 | 100 |
| 30.1 | 10 |
| 36 | 10 |

EXAMPLES

Those skilled in the art will recognize that there are a variety of methods available to prepare molecules represented in the claims. A variety of the methods known in the art have been used to prepare compounds of the invention, some of which are exemplified in the examples.

Example 1: Synthesis of 3-[2-amino-6-(1-{[6-(2-hydroxypropan-2-yl)pyridin-2-yl]methyl}-1H-1,2,3-triazol-4-yl)pyrimidin-4-yl]-2-methylbenzonitrile (Compound I)

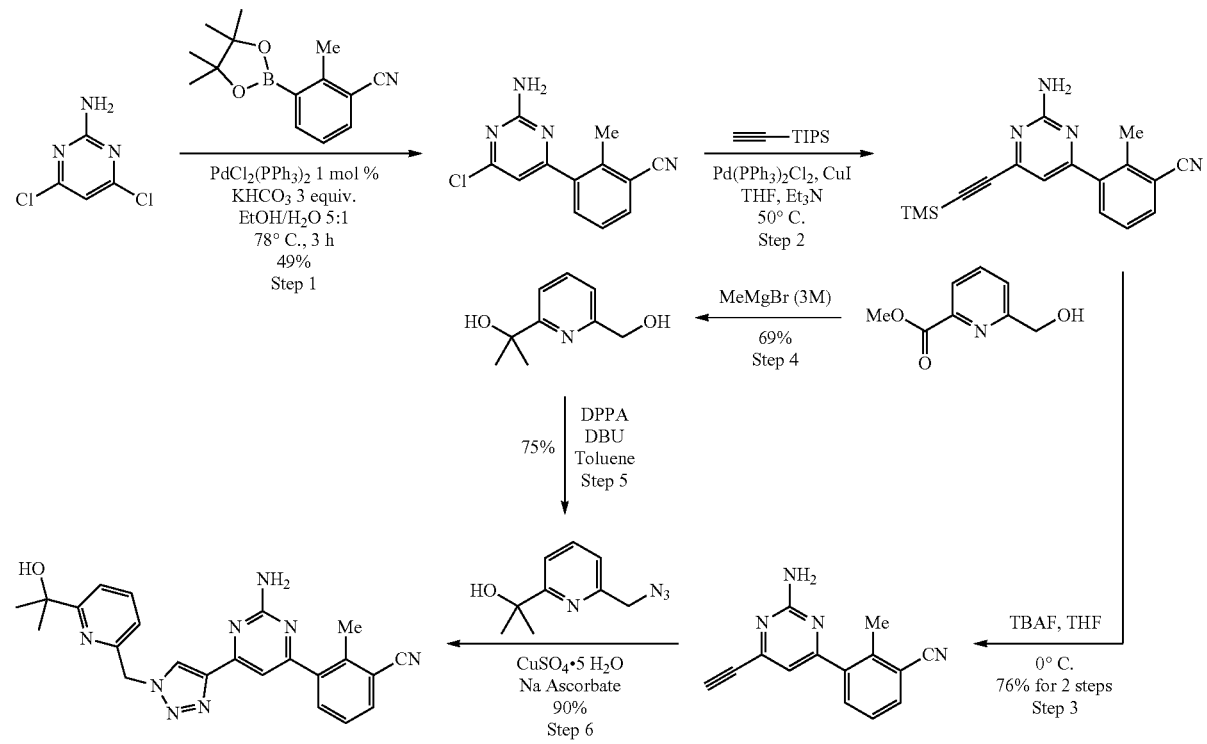

Step 1: In a 250 mL round bottom flask equipped with a magnetic stir bar was successively charged the boronic ester (3.89 g, 16 mmol) and the 2-amino-4,6-dichloropyrimidine (3.67 g, 22.4 mmol). Absolute ethanol (100 mL) was added followed by a solution of KHCO$_3$ (4.81 g, 48 mmol) in deionized water (19 mL). The resulting suspension was degassed with nitrogen for 5 minutes. PdCl$_2$(PPh$_3$)$_2$ (112 mg, 1 mol %) was then added and the mixture was heated to 78° C. for 3 hours under a nitrogen atmosphere. Ethanol was evaporated under reduced pressure and deionized water (150 mL) was added. The suspension was filtered and the solid was washed with additional water (100 mL). The solid was then dissolved in acetone (220 mL) and collected in a 500 mL round bottom flask. A mixture of silica and celite (1:1, 150 g) was added and the solvent was removed under reduced pressure. The resulting crude material was purified by flash chromatography over silica gel (dichloromethane/ethyl acetate gradient 0% to 15%). The desired product was obtained as a white solid (1.91 g, 49%). LCMS: Method A, retention time=2.93 min, ESI MS [M+H]$^+$ for C$_{12}$H$_9$ClN$_4$, calcd 245.7, found 245.2.

Step 2: In a round-bottom flask 5.1 g (20.8 mmol) of chloro-pyrimidine was suspended in 42 mL of degassed THF. To this suspension was added 8.68 mL (62.4 mmol) of Et$_3$N and 5.95 mL (25.0 mmol) of TIPS-acetylene. The reaction mixture was stirred for 5 min, followed by addition of 219 mg (0.312 mmol) of PdCl$_2$(PPh$_3$)$_2$ and 119 mg (0.624 mmol) of CuI. The reaction mixture was stirred at 50° C. for 5 h under N$_2$. After cooling the reaction to room temp., solvent was removed and the crude material was resuspended in 100 mL EtOAc from which insoluble solid was filtered off. The filtrate was washed with (1:1) NH$_4$Cl/NH$_4$OH (2×100 mL) and 10% Na$_2$S$_2$O$_4$ (1×100 mL). The organic layer was dried using Na$_2$SO$_4$, concentrated and taken to next step without further purification.

Step 3: In a round-bottom flask the crude TIPS product from previous step was dissolved in 42 mL dry THF and cooled to 0° C. To this was added 25 mL (25.0 mmol) of TBAF (1.0 M in THF). The reaction was stirred at 0° C. for 15 min. Saturated NH$_4$Cl (100 mL) was added to quench the reaction. The organics were extracted from the aqueous layer with EtOAc (2×100 mL). The combined organic layer was washed with (1:1) NH$_4$Cl/NH$_4$OH (2×100 mL) and 10% Na$_2$S$_2$O$_4$ (1×100 mL). The organic layer was dried using Na$_2$SO$_4$, concentrated and the pure product 5 was obtained by triturating with 40% CH$_2$Cl$_2$/Hexane as a light brown solid. Yield: 3.71 g (76%, 2-steps).

Step 4: To a solution of methylmagnesium bromide (3 M in Et$_2$O, 40 mL, 120 mmol, 4.0 equiv) at 0° C. under N$_2$ was added a solution of methyl 2-(hydroxymethyl)pyridine-2-carboxylate (5.0 g, 29.9 mmol) in THF (70 mL, 0.4 M) over the course of 30 minutes. The resulting mixture was allowed to warm to room temperature and stirred for 3 h. The reaction mixture was quenched with NH$_4$Cl aq (55 mL) and EtOAc (50 mL) was added. The organic phase was separated, and the aqueous phase was extracted with EtOAc (3×40 mL). The combined organic extracts were washed with saturated aqueous sodium bisulfite (7×20 mL), then dried (Na$_2$SO$_4$), filtered and concentrated in vacuo to give the title compound (3.45 g, 69% yield; 96% purity as judged by LCMS) as a pale yellow liquid. LCMS: Method A, retention time=0.722 and 1.06 min, ESI MS [M+H]$^+$ for C$_9$H$_{13}$NO$_2$, calcd 167.09, found 167.2.

Step 5: To a solution of 2-hydroxymethyl-6-(1-hydroxy-1-methylethyl)pyridine (5 g, 29.9 mmol, 1.0 equiv) in PhMe (33 mL, 0.9 M) at 0° C. under N$_2$ was added diphenylphosphoryl azide (7.73 mL, 35.9 mmol, 1.2 equiv.), followed by 1,8-diazabicyclo[5.4.0]undec-7-ene (5.37 mL, 35.9 mmol, 1.2 equiv.). The resulting mixture was to warm to room temperature and stirred for 14 h. Upon completion, diluted with ethyl acetate and washed with water, the organic layer was dried (Na$_2$SO$_4$), filtered and concentrated. The residue was dissolved in 1N aq HCl (2 eq, 60 mmol) and extracted with MTBE in hexanes (3:7, 100 mL), the organic layer was washed with water (50 mL) and the combined aqueous layer was neutralized with 2N aqueous NaOH and extracted with ethyl acetate (3×75 mL), dried the organic layer (Na$_2$SO$_4$), filtered through a plug of cotton and concentrated the filtrate to afford the pure compound as pale yellow color liquid (3.75 g, 75%). LCMS: Method A, retention time=2.67 min, ESI MS [M+H]$^+$ for C$_9$H$_{12}$N$_4$O, calcd 193.1, found 193.2.

Step 6: A mixture of azide (3.34 g, 17.4 mmol), alkyne (3.71 g, 15.8 mmol), copper(II) sulfate (39 mg; 0.158 mmol), and sodium ascorbate (156 mg, 0.790 mmol) in 2:1 t-BuOH/H$_2$O (158 mL) was heated at 60° C. for 13 h. The solvent was removed in vacuo, the residue dry loaded onto silica gel, and purified by silica gel chromatography (0-100% EtOAc in hexanes) to afford the desired product as an off-white solid (6.08 g, 90%). $^1$H NMR (400 MHz, DMSO-d$_6$) δ 8.69 (s, 1H), 7.90 (d, J=7.8 Hz, 1H), 7.80 (t, J=7.8 Hz, 1H), 7.76 (d, J=7.8 Hz, 1H), 7.61 (d, J=8.0 Hz, 1H), 7.51 (t, J=7.8 Hz, 1H), 7.28 (s, 1H), 7.10 (d, J=7.6 Hz, 2H), 6.90 (s, 2H), 5.81 (s, 2H), 5.23 (s, 1H), 2.55 (s, 3H), 1.38 (s, 6H). ESI MS [M+H]$^+$ for C$_{23}$H$_{23}$N$_8$O, calcd 427.2, found 427.3.

Example 2: Preparation of Crystalline Solid Form of 3-[2-amino-6-(1-{[6-(2-hydroxypropan-2-yl)pyridin-2-yl]methyl}-1H-1,2,3-triazol-4-yl)pyrimidin-4-yl]-2-methylbenzonitrile The product from Example 1, Step 6 (7.53 g) was dissolved in acetone (109 mL) by heating to reflux at which point water (218 mL) was added at a rate of 10 mL/min to initiate crystallization. The mixture was cooled and the solids were collected by filtration, washed with 1:2 acetone/water (109 mL), and dried under vacuum to afford Form I of Compound I as a white solid (7.08 g; 94%).

Example 3: Screening of Solid Forms of 3-[2-amino-6-(1-{[6-(2-hydroxypropan-2-yl)pyridin-2-yl]methyl}-1H-1,2,3-triazol-4-yl)pyrimidin-4-yl]-2-methylbenzonitrile Amorphous Compound I was produced by dissolving Compound I in 1,4-dioxane and subsequent lyophilization. The amorphous solid form was confirmed by the lack of indicative peaks by XRPD. To the amorphous Compound I, solvent was added to the 12×40 mg samples to prepare slurries for thermal cycling. The material was readily soluble in many of the 12 solvents and therefore, several of the samples were thermally cycled as saturated solutions.

TABLE 5

Qualitative dissolution data for amorphous Compound I

| Sample | Solvent | Solvent Added (µL) | Slurry or Solution |
|---|---|---|---|
| 1 | 25% Acetone/75% water | 200 | Solution |
| 2 | 25% MeCN/75% water | 300 | Slurry |
| 3 | 1,4-Dioxane | 200 | Solution |
| 4 | 2-Ethoxyethanol | 200 | solution |
| 5 | Isopropanol | 400 | Slurry |

TABLE 5-continued

Qualitative dissolution data for amorphous Compound I

| Sample | Solvent | Solvent Added (μL) | Slurry or Solution |
|---|---|---|---|
| 6 | acetonitrile | 400 | Slurry |
| 7 | dichloromethane | 200 | Solution |
| 8 | Isopropyl acetate | 200 | Solution |
| 9 | Methanol | 200 | Solution |
| 10 | THF | 200 | Solution |
| 11 | Toluene | 700 | Slurry |
| 12 | water | 700 | slurry |

Slurries/solutions were then thermally cycled (with agitation) for ~72 h—r.t. for 4 h then 40° C. for 4 h. Any solid material remaining post-temperature cycle was filtered and the isolated material was analyzed by XRPD and PLM. TG/DTA was also collected on any crystalline material; where material amounts allowed. The 12 saturated solutions remaining, either post-filtration or if no solid material was present, were split evenly into 3 and the following were carried out:

Crash cooling at ~2° C.—vial placed in a refrigerator overnight.

Anti-solvent addition—1 mL of anti-solvent was added (tBME) and the sample was left overnight. Where no solid was isolated, the solvent was evaporated and the material redissolved in its original solvent before adding 1 mL of tBME or heptane as anti-solvent. The sample was left overnight.

Evaporation—the cap was removed from the vial to allow solvent evaporation to occur.

Any solids isolated at this stage were analyzed by XRPD, PLM and if crystalline, TG/DTA was collected (where material amounts allowed).

Post-thermal cycle, the following solvents produced transparent solutions with no solid material: 1,4-dioxane, 2-ethoxyethanol and THF.

Form I of Compound I was produced from 25% acetone: 75% water; dichloromethane; and toluene. An exemplary XRPD of Form I is shown in FIG. 1 with the peak listing as shown in Table 1.

Figure 6:
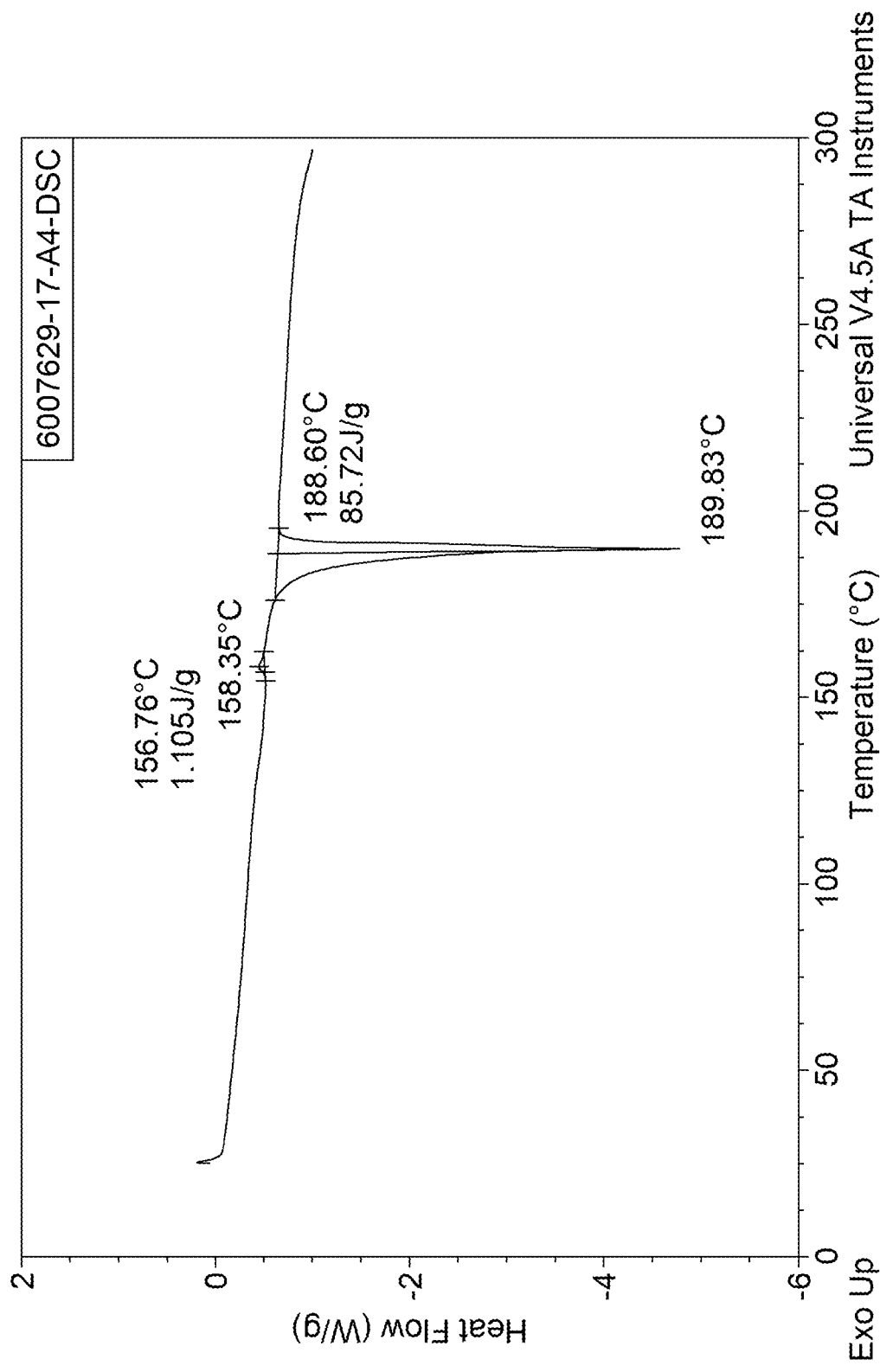
FIG. 6 shows a differential scanning calorimetry (DSC) plot of Compound I Form II.

Form II of Compound I, having an XRPD in accordance with FIG. 5 and a DSC pattern in accordance with FIG. 6, was produced from 25% acetonitrile:75% water. The peak listing for the XRPD of Form II in FIG. 5 is shown in Table 3.

Form III of Compound I was produced from the isopropanol, acetonitrile, methanol, and water samples. Form III has an XRPD in accordance with those shown in FIG. 7 and a DSC pattern in accordance with FIG. 8. The peak listing for the XRPD of Form III in FIG. 7 is shown in Table 4.

Example 4: Additional Exemplary Crystallization Conditions of Compound I

Using methods of single solvent heating, binary solvent mixture heating, and slow evaporation, a variety of conditions were identified which yielded crystalline forms of the material. Crystallinity was initially determined through the melting range of the material, in which crystalline compounds exhibit relatively sharp and higher melting ranges compared the amorphous material. Amorphous material obtained through lyophilization exhibited a melting range of <100° C. Summaries of selected conditions are shown in Tables 6 and 7.

TABLE 6

Crystallization via Use of Single Solvents via Heating/Cooling or Slow Evaporation

| Solvent | Heating/Cooling | Slow Evaporation |
|---|---|---|
| Methyl tert-butyl ether | 178-181* | 176-178 |
| Diethyl ether | — | 176-178 |
| Isobutyl acetate | 178-181* | — |
| Ethyl acetate | 178-181* | 193-195 |
| Methyl ethyl ketone | 178-181* | 178-180 |
| Acetone | 194-196 | 178-181* |
| Isopropanol | 178-180* | 193-196 |
| Ethanol | 178-180* | 193-196 |

Melting points in ° C.
*Second melting occurs at about 193-194° C.

TABLE 7

Crystallization via Use of Binary Solvent Mixtures

| | Anti-Solvent | | | | | | |
|---|---|---|---|---|---|---|---|
| Solvent | Pentane | Heptane | Methyl tert-butyl ether | Ether | Isobutyl acetate | Methyl ethyl ketone | Water |
| Isobutyl acetate | 193-194 | 178-180* | 178-181* | 178-181* | — | — | — |
| Ethyl acetate | 193-195 | 193-195 | 193-195 | 179-181* | — | — | — |
| 2-Butanone | 193-195 | 193-195 | 193-195 | 193-195 | 193-195 | — | — |
| Acetone | 194-196 | 194-196 | 194-196 | 179-181* | — | — | 194-196 |
| Isopropanol | 180-181* | 193-194 | — | 180-181* | 178-180* | 193-195 | 178-180 |
| Ethanol | 178-180 | 178-180 | — | — | — | — | 178-180 |
| DMSO | — | — | — | 192-193 | — | — | 190-193 |

Melting points in ° C.
*Second melting occurs at about 193-194° C.

Melting point measurements on the material obtained from different solvent combinations suggest at least two crystalline forms of the material can be obtained. The highest melting form (Form I) observed melted approximately at 193-195° C. and was generally obtained from binary mixtures. An additional form (Form III) melting at 179-181° C. was also observed which was generally obtained through use of binary mixtures containing an alcohol solvent or use of a single solvent. Frequently, partial melting at 179-181° C. was observed, followed by the remainder of the solid melting at 193-195° C. Additionally, in certain samples, complete melting at 179-181° C. was observed, followed by resolidification and a second melting at 193-195° C. NMR analyses of select batches showed only trace amounts of solvent present.

Confirmation of the differences in morphology was obtained through XRPD and DSC analyses. XRPD analysis showed two distinct patterns for the respective crystalline forms. DSC data was also consistent with the melting points observed.

Form I (melting point 193-195° C.) is a more thermally stable polymorph based on DSC data indicating the phase transition occurs at 194° C. as compared to Form III which has a transition that occurs at 178° C. Competitive 1:1 slurry experiments of the two forms provided additional support for the stability as Form III converted to Form I in a variety of solvents.

Example 5: Single Crystal X-Ray Diffraction of Form I of Compound I

The single crystal X-ray diffraction studies were carried out on a Bruker Kappa APEX-II CCD diffractometer equipped with Mo K$_\alpha$ radiation ($\lambda$=0.71073 Å). A 0.253× 0.227×0.206 mm piece of a colorless block was mounted on a Cryoloop with Paratone oil. Data were collected in a nitrogen gas stream at 100(2) K using $\phi$ and $\overline{\omega}$ scans. Crystal-to-detector distance was 40 mm and exposure time was 4 seconds per frame using a scan width of 2.0°. Data collection was 100% complete to 25.00° in $\theta$. A total of 33406 reflections were collected covering the indices, $-17 \leq h \leq 18$, $-25 \leq k \leq 25$, $-7 \leq l \leq 9$. 4373 reflections were found to be symmetry independent, with a $R_{int}$ of 0.0474. Indexing and unit cell refinement indicated a primitive, monoclinic lattice. The space group was found to be P2$_1$/c. The data were integrated using the Bruker SAINT software program and scaled using the SADABS software program. Solution by direct methods (SHELXT) produced a complete phasing model consistent with the proposed structure. The single crystal X-ray diffraction data for Compound I Form I is shown in Table 2.

All nonhydrogen atoms were refined anisotropically by full-matrix least-squares (SHELXL-2014). All carbon bonded hydrogen atoms were placed using a riding model. Their positions were constrained relative to their parent atom using the appropriate HFIX command in SHELXL-2014. All other hydrogen atoms (H-bonding) were located in the difference map. Their relative positions were restrained using DFIX commands and their thermals freely refined.

Example 6: Stability and Hygroscopicity of Form I of Compound I

Vials containing a quantity of Form I of Compound I were subjected to a temperature of 40° C. at 75% relative humidity (RH) for one week. Analysis by HPLC and XRPD indicated the crystalline material was stable with no decomposition or morphology change observed. Additionally, vials containing a quantity of the crystalline material were subjected to a temperature of 80° C. in a closed vial for one week. Analysis by HPLC and XRPD indicated the crystalline material was stable with no decomposition or change in morphology observed.

Figure 4:
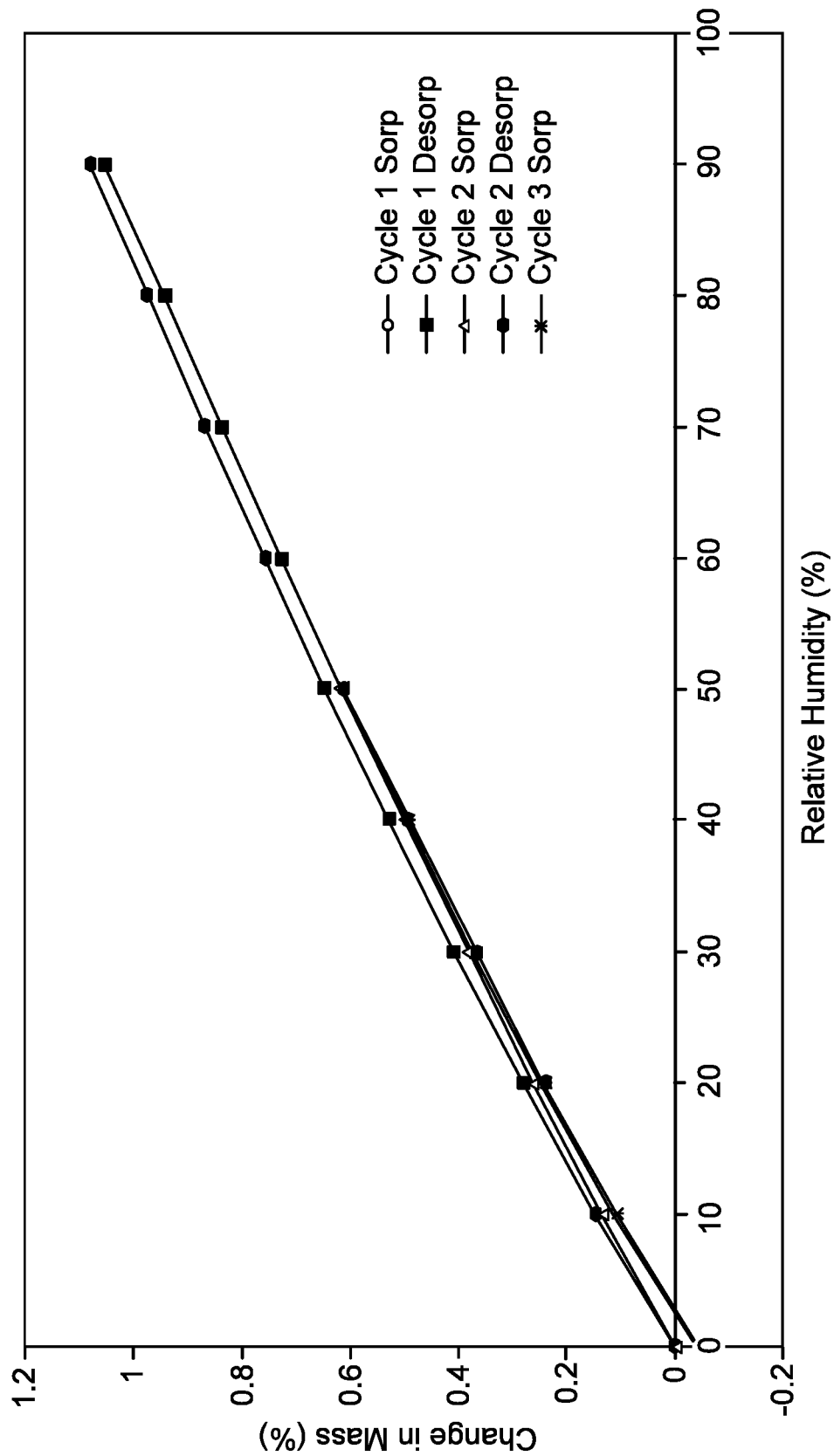
FIG. 4 shows a dynamic vapor sorption (DVS) isotherm plot of Compound I Form I.

A quantity of Compound I Form I was analyzed by dynamic vapor sorption (DVS). The sample was subjected to a ramping profile from 40-90% RH at 10% increments, maintaining the sample at each step until a stable weight had been achieved at 25° C. After completion of the sorption cycle, the sample was dried using the same procedure to 0% RH and then a second sorption cycle back to 40% RH. Two cycles were performed. The weight change during the sorption/desorption cycles were plotted, allowing for the hygroscopic nature of the sample to be determined. XRPD analysis was then carried out on the resultant solid, with no change in morphology observed. DVS showed reversible absorption of water in the 0-90% relative humidity range with a maximum value of 1.1% water at 90% relative humidity as shown in FIG. 4. This value indicates a slightly hygroscopic material but below the theoretical monohydrate value of 4.22%. No hysteresis was observed upon cycling the material.

Particular embodiments of this invention are described herein, including the best mode known to the inventors for carrying out the invention. Upon reading the foregoing description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference as if each individual publication or patent application were specifically and individually indicated to be incorporated by reference.

What is claimed is:

1. A solid form of Compound I:

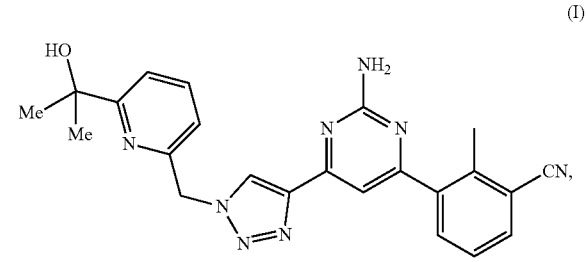 [SMILES: Cc1c(C#N)cccc1-c1cc(-c2cn(Cc3cccc(C(C)(C)O)n3)nn2)nc(N)n1]

wherein the solid form is characterized by an XRPD pattern comprising one or more peaks at 6.9, 8.0, 8.2, 12.5, 12.7, 14.8, 15.0, 15.7, 16.8, 18.1, 18.8, 19.2, 20.6, 21.1, 21.8, 24.9, 27.1, or 27.7 degrees 2θ (±0.1 degrees 2θ), wherein the XRPD is made using CuKα1 radiation, or a hydrate or solvate thereof.

2. The solid form of claim 1, characterized by an XRPD pattern comprising peaks at 6.9, 8.2, and 15.7 degrees 2θ (±0.1 degrees 2θ), wherein the XRPD is made using CuKα1 radiation.

3. The solid form of claim 2, further comprising one or more peaks at 14.8, 15.0, 18.8, or 21.1 degrees 2θ (±0.1 degrees 2θ), wherein the XRPD is made using CuK$_{\alpha 1}$ radiation.

4. The solid form of claim 1, characterized by an X-ray powder diffraction pattern (XRPD) having peaks at 6.9, 8.0, 8.2, 12.5, 12.7, 14.8, 15.0, 15.7, 16.8, 18.1, 18.8, 19.2, 20.6, 21.1, 21.8, 24.9, 27.1, and 27.7 degrees 2θ (±0.1 degrees 2θ), wherein the XRPD is made using CuK$_{\alpha 1}$ radiation.

5. The solid form of claim 1, characterized by an X-ray powder diffraction pattern (XRPD) substantially in accordance with that of FIG. 1.

6. The solid form of claim 1, characterized by a unit cell as determined by single crystal X-ray crystallography of the following dimensions: a=15.1880 (7)Å; b=20.9125 (11)Å; c=7.5242 (4)Å; α=90°; β=90.7720 (10) °; and γ=90°.

7. The solid form of claim 1, characterized by a differential scanning calorimetry (DSC) pattern having an endotherm at about 193° C.

8. The solid form of claim 1, characterized by a differential scanning calorimetry (DSC) pattern substantially in accordance with that of FIG. 2.

9. A pharmaceutical composition comprising a solid form of claim 1 and a pharmaceutically acceptable excipient.

10. A method of treating a disease, disorder, or condition, mediated at least in part by the adenosine $A_{2A}$ receptor ($A_{2A}R$) or the adenosine $A_{2B}$ receptor ($A_{2B}R$), or both the $A_{2A}R$ and $A_{2B}R$ receptors, said method comprising administering a therapeutically effective amount of a solid form of claim 1 to a subject in need thereof.

11. The method of claim 10, wherein said disease, disorder, or condition is cancer, or an immune-related disease, disorder or condition.

12. The method of claim 11, wherein said cancer is a cancer of the prostate, colon, rectum, pancreas, cervix, stomach, endometrium, brain, liver, bladder, ovary, testis, head, neck, skin, mesothelial lining, white blood cell, esophagus, breast, muscle, connective tissue, lung, adrenal gland, thyroid, kidney, or bone; or is glioblastoma, mesothelioma, renal cell carcinoma, gastric carcinoma, sarcoma, choriocarcinoma, cutaneous basocellular carcinoma, or testicular seminoma.

13. The method of claim 11, further comprising administering at least one additional therapeutic agent to the subject in need thereof.

14. The method of claim 13, wherein said at least one additional therapeutic agent comprises an immune checkpoint inhibitor that blocks the activity of at least one of PD-1, PD-L1, TIGIT, or CTLA-4.

15. The method of claim 11, wherein said cancer is non-small-cell lung carcinoma.

16. The method of claim 11, wherein said cancer is prostate cancer.

17. The method of claim 11, wherein said cancer is colon cancer or rectal cancer.

18. The method of claim 11, wherein said cancer is pancreatic cancer.

19. A solid form of Compound I:

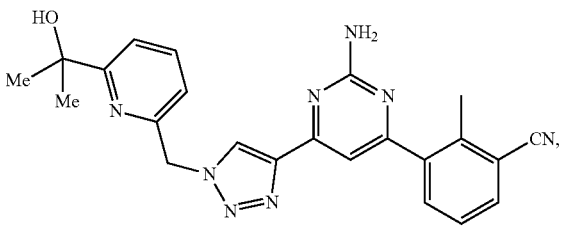

(I)

characterized by an X-ray powder diffraction pattern (XRPD) substantially in accordance with that of FIG. 5.

20. A solid form of Compound I,

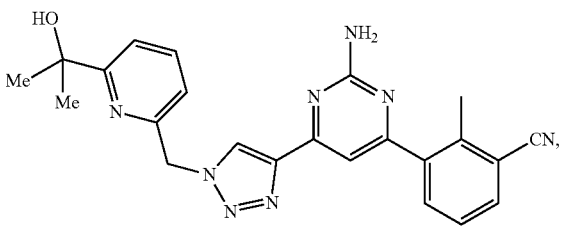

(I)

characterized by an X-ray powder diffraction pattern (XRPD) substantially in accordance with that of FIG. 7.

21. The method of claim 11, wherein said cancer is melanoma, basal cell carcinoma, lymphoma, leukemia, small-cell lung carcinoma, or Kaposi's sarcoma.

* * * * *